US007981414B2

(12) United States Patent
Woolven et al.

(10) Patent No.: US 7,981,414 B2
(45) Date of Patent: Jul. 19, 2011

(54) ANTI-INFLAMMATORY DAB

(75) Inventors: Benjamin P. Woolven, Cambridgeshire (GB); Ian M. Tomlinson, Cambridgeshire (GB); Jennifer A. Lee, Cambridgeshire (GB); Anthony G. Doyle, Drummoyne (AU); Philip A. Jennings, Warrawee (AU)

(73) Assignee: Cephalon Australia Pty Ltd, Macquarie Park, NSW (AU)

( * ) Notice: Subject to any disclaimer, the term of this patent is extended or adjusted under 35 U.S.C. 154(b) by 0 days.

(21) Appl. No.: 11/659,009

(22) PCT Filed: Dec. 20, 2006

(86) PCT No.: PCT/AU2006/001940
§ 371 (c)(1),
(2), (4) Date: Jan. 30, 2007

(87) PCT Pub. No.: WO2007/070948
PCT Pub. Date: Jun. 28, 2007

(65) Prior Publication Data
US 2009/0226428 A1    Sep. 10, 2009

Related U.S. Application Data

(60) Provisional application No. 60/817,272, filed on Jun. 28, 2006.

(30) Foreign Application Priority Data

Dec. 20, 2005   (AU) ................................ 2005907124

(51) Int. Cl.
A61K 39/00     (2006.01)
A61K 39/395    (2006.01)
C12P 21/08     (2006.01)
C07K 16/00     (2006.01)

(52) U.S. Cl. ............... 424/133.1; 424/158.1; 530/387.3; 530/388.24

(58) Field of Classification Search ........................ None
See application file for complete search history.

(56) References Cited

U.S. PATENT DOCUMENTS

| | | | |
|---|---|---|---|
| 5,994,510 | A | 11/1999 | Adair |
| 6,821,505 | B2 | 11/2004 | Ward |
| 7,141,653 | B2 | 11/2006 | Greenfeder |
| 2003/0118592 | A1 | 6/2003 | Ledbetter et al. |
| 2003/0143682 | A1 | 7/2003 | Nicolaides et al. |
| 2003/0199679 | A1 | 10/2003 | Adair |
| 2004/0101905 | A1 | 5/2004 | Brekke |
| 2004/0132101 | A1 | 7/2004 | Lazar |
| 2005/0226863 | A1 | 10/2005 | Colby |
| 2005/0271663 | A1* | 12/2005 | Ignatovich et al. ........ 424/145.1 |
| 2006/0024308 | A1 | 2/2006 | Crea |
| 2006/0034845 | A1 | 2/2006 | Silence |
| 2006/0038027 | A1 | 2/2006 | O'Conner |
| 2006/0073141 | A1 | 4/2006 | Ignatovich et al. |
| 2006/0083747 | A1 | 4/2006 | Winter |
| 2007/0003549 | A1 | 1/2007 | Ignatovich et al. |
| 2007/0111281 | A1 | 5/2007 | Sondermann |
| 2007/0202105 | A1 | 8/2007 | Doyle et al. |
| 2007/0269449 | A1 | 11/2007 | Walczak |
| 2008/0071063 | A1 | 3/2008 | Allan |
| 2008/0095767 | A1 | 4/2008 | Jennings et al. |
| 2008/0139790 | A1 | 6/2008 | Jennings et al. |
| 2008/0227958 | A1 | 9/2008 | Thompson |
| 2008/0241166 | A1 | 10/2008 | Tomlinson et al. |
| 2008/0255343 | A1 | 10/2008 | Jennings et al. |
| 2008/0260738 | A1 | 10/2008 | Moore |
| 2009/0075338 | A1 | 3/2009 | Moore |
| 2009/0081233 | A1 | 3/2009 | Ignatovich et al. |
| 2009/0148905 | A1 | 6/2009 | Ashman |
| 2009/0221803 | A1 | 9/2009 | Dall'Acqua |
| 2009/0258012 | A1 | 10/2009 | Ignatovich et al. |
| 2009/0286962 | A1 | 11/2009 | Woolven et al. |

FOREIGN PATENT DOCUMENTS

| | | |
|---|---|---|
| WO | WO 88/01649 | 3/1988 |
| WO | WO-93/02108 A1 | 2/1993 |
| WO | WO 97/34631 | 9/1997 |
| WO | WO 00/42072 | 7/2000 |
| WO | WO 2004/058820 | 7/2004 |
| WO | WO 2004/058821 | 7/2004 |
| WO | WO 2004/058822 | 7/2004 |
| WO | WO-2005/003345 A2 | 1/2005 |
| WO | WO-2005/003345 A3 | 1/2005 |
| WO | WO-2005/035572 A2 | 4/2005 |
| WO | WO-2005/035572 A3 | 4/2005 |
| WO | WO-2005/047325 A2 | 5/2005 |
| WO | WO-2005/047325 A3 | 5/2005 |
| WO | WO 2005/063816 | 7/2005 |
| WO | WO-2006/003388 A2 | 1/2006 |
| WO | WO-2006-003388 A3 | 1/2006 |
| WO | WO 2006003388 A2 * | 1/2006 |
| WO | WO-2006/096653 A2 | 9/2006 |
| WO | WO-2007/070979 A1 | 6/2007 |

(Continued)

OTHER PUBLICATIONS

Skolnick and Fetrow. From genes to protein structure and function: novel applications of computational approaches in the genomic era. Trends in Biotechnology, 2000. vol. 18, pp. 34-39.*

Burgess, Shaheen, Ravera, Jaye, Donohue, and Winkles. Possible dissociation of the heparin binding and mitogenic activities of heparin binding (acidic fibroblast) growth factor 1 from its receptor binding activities by site directed mutagenesis of a single lysine residue. Journal of Cell Biology, 1990. vol. 111, pp. 2129-2138.*

Lazar, Watanabe, Dalton, and Sporn. Transforming growth factor alpha: mutation of aspartic acid 47 and leucine 48 results in different biological activities. Molecular and Cellular Biology, 1988. vol. 8, pp. 1247-1252.*

Harmsen and Haard. Properties, production and applications of camelid single domain antibody fragments. Appl. Microbiol. Biotechnol. 2007, vol. 77, pp. 13-22.*

Muyldermans and Lauwereys. Unique single domain antigen binding fragments derived from naturally occurring camel heavy chain antibodies. Journal of Molecular Recognition, 1999. vol. 12, pp. 131-140.*

(Continued)

Primary Examiner — Anne M. Gussow

(57) ABSTRACT

The present invention provides a recombinant domain antibody (dAb) which binds to human TNF-α, the dAb comprising an immunoglobulin heavy or light chain variable domain, wherein the variable domain comprises at least one complementarity determining region (CDR) having a sequence derived from a New World primate.

10 Claims, 11 Drawing Sheets

FOREIGN PATENT DOCUMENTS

| WO | WO 2009/006520 | 1/2009 |
|---|---|---|
| WO | WO 2009/134776 | 11/2009 |
| WO | WO 2009/143472 | 11/2009 |

OTHER PUBLICATIONS

Brekke, O.H. et al. (1995). "The Structural Requirements for Complement Activation by IgG: Does it Hinge on the Hinge?," *Immunology Today* 16(2):85-90.

Davies, J. et al. (1996). "Affinity Improvement of Single Antibody VH Domains: Residues in all Three Hypervariable Regions Affect Antigen Binding," *Immunotechnology* 2:169-179.

Foote, J. et al. (1992). "Antibody Framework Residues Affecting the Conformation of the Hypervariable Loops," *J. Mol. Biol.* 224:487-499.

Hwang, W.Y.K. et al. (2005). "Use of Human Germline Genes in a CDR Homolgy-Based Approach to Antibody Humanization," *Methods* 36:35-42.

Jones, P.T. et al. (May 29, 1986). "Replacing the Complementarity-Determining Regions in a Human Antibody with those from a Mouse," *Nature* 321:522-525.

Non-Final Office Action mailed Nov. 4, 2009, for U.S. Appl. No. 11/670,261, filed Feb. 1, 2007, 12 pages.

Reiter, Y. et al. (1999). "An Antibody Single-Domain Phage Display Library of a Native Heavy Chain Variable Region: Isolation of Functional Single-Domain VH Molecules with a Unique Interface," *J. Mol. Biol.* 290:685-698.

Rudikoff, S. et al. (Mar. 1982). "Single Amino Acid Substitution Altering Antigen-Binding Specificity," *Proc. Natl. Acad. Sci. USA* 79:1979-1983.

Saerens, D. et al. (2005, e-pub. Jul. 25, 2005). "Identification of a Universal VHH Framework to Graft Non-canonical Antigen-binding Loops of Camel Single-domain Antibodies," *J. Mol. Biol.* 352:597-607.

Schneider, W.P. et al. (Apr. 1988). "Genetically Engineered Immunoglobulins Reveal Structural Features Controlling Segmental Flexibility," *Proc. Natl. Acad. Sci. USA* 85:2509-2513.

Supplementary European Search Report mailed Jun. 18, 2009, for EP Application No. 06828046.0, nine pages.

Demarest, S.J. et al. (Sep. 2008). "Antibody Therapeutics, Antibody Engineering, and the Merits of Protein Stability," *Curr. Opin. Drug Discov. Devel.* 11(5):675-687. (Abstract Only.).

Martin, A.C.R. (2008). "The Kabat Numbering Scheme," located at <http://www.bioinf.org.uk/abs/>, last visited Mar. 9, 2008, eight pages.

Paz, K. et al. (Nov. 2005). "Human Single-Domain Neutralizing Intrabodies Directed Against Etk Kinase: A Novel Approach to Impair Cellular Transformation," *Mo. Cancer Ther.* 4(11):1801-1809.

Brorson, K. et al. (1999). "Mutational Analysis of Avidity and Fine Specificity of Anti-Levan Antibodies," *The Journal of Immunology* 163:6694-6701.

Brummell, D.A. et al. (Feb. 1993). "Probing the Combining Site of an Anti-Carbohydrate Antibody by Saturation-Mutagenesis: Role of the Heavy-Chain CDR3 Residues," *Biochemistry* 32:1180-1187 (Abstract from PubMed only.).

Burks, E.A. et al. (Jan. 1997). "In Vitro Scanning Saturation Mutagenesis of an Antibody Binding Pocket," *Proc. Natl. Acad. Sci. USA* 94:412-417.

Casset, F. et al. (2003). "A Peptide Mimetic of an Anti-CD4 Monoclonal Antibody by Rational Design," *Biochemical and Biophysical Research Communications* 307:198-205.

Chen, Y. et al. (1999). "Selection and Analysis of an Optimized Anti-VEGF Antibody: Crystal Structure of an Affinity-Matured Fab in Complex with Antigen," *J. Mol. Biol.* 293:865-881.

Colman, P.M. (1994). "Effects of Amino Acid Sequence Changes on Antibody-Antigen Interactions," *Research in Immunol.* 145:33-36.

De Pascalis, R. et al. (2002). "Grafting of 'Abbreviated' Complementarity-Determining Regions Containing Specificity-Determining Residues Essential for Ligand Contact to Engineer a Less Immunogenic Humanized Monoclonal Antibody," *The Journal of Immunology* 169:3076-3084.

Dufner, P. et al. (2006, e-pub. Sep. 26, 2006). "Harnessing Phage and Ribosome Display for Anti-body Optimisation," *Trends Biotechnol.* 24(11):523-529.

Holm, P. et al. (2007). "Functional Mapping and Single Chin Construction of the Anti-Cytokeratin 8 Monoclonal Antibody TS1," *Mol. Immunol.* 44:a1075-1084.

Jang, Y.-J. et al. (1998). "The Structural Basis for DNA Binding by an Anti-DNA Autoantibody," *Mol. Immunol.* 35:1207-1217.

Kobayashi, H. et al. (1999). "Tryptophan H33 Plays an Important Role in Pyrimidine (6-4) Pyrimidone Photoproduct Binding by a High-Affinity Antibody," *Protein Engineering* 12(10):879-884.

Kumar, S. et al. (Nov. 10, 2000). "Molecular Cloning and Expression of the Fabs of Human Autoantibodies in *Escherichia coli*," *J. Biol. Chem.* 275(45):35129-35136.

MacCallum, R.M. et al. (1996). "Antibody-Antigen Interactions: Contact Analysis and Binding Site Topography," *J. Mol. Biol.* 262:732-745.

Non-Final Office Action mailed Oct. 29, 2008, for U.S. Appl. No. 11/636,338, filed Dec. 8, 2006, 25 pages.

Smith-Gill, S.J. et al. (Dec. 15, 1987). "Contributions of Immunoglobulin Heavy and Light Chains to Antibody Specificity for Lysozyme and Two Haptens," *The Journal of Immunology* 139(12):4135-4144.

Song, M-K. et al. (2000). "Light Chain of Natural Antibody Plays a Dominant Role in Protein Antigen Binding," *Biochemical and Biophysical Research Communications* 268(2):390-394.

Vajdos, F.F. et al. (2002). "Comprehensive Functional Maps of the Antigen-Binding Site of an Anti-ErbB2 Antibody Obtained with Shotgun Scanning Mutagenesis," *J. Mol. Biol.* 320:415-428.

Wu, H. et al. (1999). "Humanization of a Murine Monoclonal Antibody by Simultaneous Optimization of Framework and CDR Residues," *J. Mol. Biol.* 294:151-162.

International Search Report mailed on Mar. 26, 2007, for PCT Application No. PCT/AU2006/001993 filed on Dec. 20, 2006, three pages.

Qi, Y. et al. (1995). "A Genetically Engineered Single-Gene-Encoded Anti-TAG72 Chimeric Antibody Secreted From Myeloma Cells," *Hum. Antibodies Hybridomas* 6(4):161-166 (Abstract only located at PubMed last visited Feb. 26, 2007, one page).

* cited by examiner

FIGURE 1

| | | | | | | | | | | | | | | | |
|---|---|---|---|---|---|---|---|---|---|---|---|---|---|---|---|
| 1 | GAC | ATC | CAG | ATG | ACC | CAG | TCT | CCA | TCC | TCT | CTG | TCT | GCA | TCT | GTA | 45 |
| 1 | Asp | Ile | Gln | Met | Thr | Gln | Ser | Pro | Ser | Ser | Leu | Ser | Ala | Ser | Val | 15 |
| 46 | GGA | GAC | CGT | GTC | ACC | ATC | ACT | TGC | CGG | GCA | AGT | CAG | AGC | ATT | GAT | 90 |
| 16 | Gly | Asp | Arg | Val | Thr | Ile | Thr | Cys | Arg | Ala | Ser | Gln | Ser | Ile | Asp | 30 |
| 91 | AGT | TAT | TTA | CAT | TGG | TAC | CAG | CAG | AAA | CCA | GGG | AAA | GCC | CCT | AAG | 135 |
| 31 | Ser | Tyr | Leu | His | Trp | Tyr | Gln | Gln | Lys | Pro | Gly | Lys | Ala | Pro | Lys | 45 |
| 136 | CTC | CTG | ATC | TAT | AGT | GCA | TCC | GAG | TTG | CAA | AGT | GGG | GTC | CCA | TCA | 180 |
| 46 | Leu | Leu | Ile | Tyr | Ser | Ala | Ser | Glu | Leu | Gln | Ser | Gly | Val | Pro | Ser | 60 |
| 181 | CGT | TTC | AGT | GGC | AGT | GGA | TCT | GGG | ACA | GAT | TTC | ACT | CTC | ACC | ATC | 225 |
| 61 | Arg | Phe | Ser | Gly | Ser | Gly | Ser | Gly | Thr | Asp | Phe | Thr | Leu | Thr | Ile | 75 |
| 226 | AGC | AGT | CTG | CAA | CCT | GAA | GAT | TTT | GCT | ACG | TAC | TAC | TGT | CAA | CAG | 270 |
| 76 | Ser | Ser | Leu | Gln | Pro | Glu | Asp | Phe | Ala | Thr | Tyr | Tyr | Cys | Gln | Gln | 90 |
| 271 | GTT | GTG | TGG | CGT | CCT | TTT | ACG | TTC | GGC | CAA | GGG | ACC | AAG | GTG | GAA | 315 |
| 91 | Val | Val | Trp | Arg | Pro | Phe | Thr | Phe | Gly | Gln | Gly | Thr | Lys | Val | Glu | 105 |
| 316 | ATC | AAA | CGG | 324 | | | | | | | | | | | | |
| 106 | Ile | Lys | Arg | | | | | | | | | | | | | |

FIGURE 2A

Marmoset Sequences

Marmoset nucleotide sequence 1 (SEQ ID No:14)
GACATCCAGATGACCCAGTCTCCATCTTCCCTGACTGCATCTGTAGGAGGCAAAGTCACCATC
ACTTGCCGGGCGAGTCAGGACATTAACAAGTGGTTAGCCTGGTATCAGCAGAAACCAGGGACA
GTCCCTAAGCCCCTGATCTATGAGGCATCCAAATTGCAAAGTGGGGTCCCATCAAGGTTCAGC
GGCAGTGGATCTGGGACATATTTTACTCTCACCATCAGCAGCCTGCAGCCTGAAGATGCTGCA
ACTTATTACTGTCAG Marmoset nucleotide sequence 2 (SEQ ID No:15)
GACATCCAGATGATCCAGTCTCCATCCTCCCTGTCTGCATCTGTAGGAGACAGAGTCACCATC
ACTTGCTGGGCAAGTCAGGGTATTAGCCACTGGTTAGCCTGGTATCAGCAGAAACCAGGGAAA
GCCCCTAAGCTCCTGATCTATAGTGCATCAAATTTAGAAACAGGGGTCCCATCAAGGTTCAGT
GGAAGTGGATCCAGGACAGATTTTACTCTCACCATCAGCAGCCTGCAGCCTGAAGATATTGCA
ACATATTACTGTCAA Marmoset nucleotide sequence 3 (SEQ ID No:16)
GACATCCAGATGACCCAGACTCCATCCTCCCTGTCTGCATCTGTAGGAGACAGAGTCACCATC
ACTTGCCGGGCAAGTCAGGGTATTAGCAGCTGGTTAGCCTGGTATCAGCAGAAACCAGGGAAA
GCCCCTAAGCTCCTGATCTATGGGGCATCAAATTTGGAAACAGGGGTCCCATCAAGATTCAGC
GGAAGTGGATCTGGGACAGATTTTACTCTCACCATCAGCAGTCTGCAGCCTGAAGATATTGCA
ACATATTACTGTCAA Marmoset nucleotide sequence 4 (SEQ ID No:17)
GACATCCAGATGATCCAGTCTCCATCCTCCCTGTCTGCATCTGTAGGAGACAGAGTCACCATC
ACTTGCTGGGCAAGTCAGGGTATTAGCCACTGGTTAGCCTGGTATCAGCAGAAACCAGGGAAA
GCCCCTAAGCTCCTGATCTATAGTGCATCAAATTTAGGAACAGGGGTCCCATCAAGGTTCAGT
GGAAGTGGATCCAGGACAGATTTTACTCTCACCATCAGCAGCCTGCAGCCTGAAGATATTGCA
ACATATTACTGTCAA Marmoset nucleotide sequence 5 (SEQ ID No:18)
GACATCCAGATGACCCAGTCTCCATCTTCCCTGACTGCATCTGTAGGAGGCAAAGTCACCATC
ACTTGCCGGGCGTGTCAGGACATTAACAAGTGGTTAGCCTGGTATCAGCAGAAACCAGGGACA
GTCCCTAAGCCCCTGATCTATGAGGCATCCAAATTGCAAAGTGGGGTCCCATCAAGGTTCAGC
GGCAGTGGATCTGGGACATATTTTACTCTCACCATCAGCAGCCTGCAGCCTGAAGATGCTGCA
ACTTATTACTGTCAG

FIGURE 2B

Marmoset nucleotide sequence 6 (SEQ ID No:19)
GACATCCAGATGACCCAGTCTCCATCCTCCCTGTCTGCATCTGTAGGAGACAGAGTTACCATC
ACTTGCCGGGCGAGTCAGGGCATTAGTAATTATTTAGCCTGGTATCAGCAGAAACCAGGGAAA
ACTCCTAGGCTCCTGATCTATGCTGCATCCAGTTTACAAACTGGGATTCCCTCTCGGTTCAGC
GGCAGTGGATCTGGGACAGACTACACTCTCACCATCAGCAGCCTGCAGTCTGAAGATGTTGCA
ATTTATTACTGTCAA

Marmoset nucleotide sequence 7 (SEQ ID No:20)
GACATCCAGATGACCCAGTCTCCATCTTCCCTGACTGCATCTGTAGGAGGCAAAGTCACCATC
ACTTGCCGGGCGAGTCAGGACATTAACAAGTGGTTAGCCTGGTATCAGCAGAAACCAGGGACA
GTCCCTAAGCCCCTGATCTATGAGGCATCCAAATTGCAAAGTGGGGTCCCATCAAGGCTCAGC
GGCAGTGGATCTGGGACATATTTCACTCTCACCATCAGCAGCCTGCAGCCTGAAGATGCTGCA
ACTTATTACTGTCAG

Marmoset nucleotide sequence 8 (SEQ ID No:21)
GACATCCAGATGACCCAGTCTCCATCTTCCCTGACTGCATCTGTAGGAGGCAAAGTCACCATC
ACTTGCCGGGCGAGTCAGGACATTAACAAGTGGTCAGCCTGGTATCAGCAGAAACCAGGGACA
GTCCCTAAGCCCCTGATCTATGAGGCATCCAAATTGCAAAGTGGGGTCCCATCAAGGTTCAGC
GGCAGTGGATCTGGGACATATTTTACTCTCACCATCAGCAGCCTGCAGCCTGAAGATGCTGCA
ACTTATTACTGTCAG

Marmoset nucleotide sequence 9 (SEQ ID No:22)
GACATCCAGATGACCCAGTCTCCATCTTCCCTGACTGCATCTGTAGGAGGCAAAGTCACCGTC
ACTTGCCGGGCGAGTCAGGACATTAACAAGTGGTTAGCCTGGTATCAGCAGAAACCAGGGACA
GTCCCTAAGCCCCTGATCTATGAGGCATCCAAATTGCAAAGTGGGGTCCCATCAAGGTTCAGC
GGCAGTGGATCTGGGACATATTTTACTCTCACCATCAGCAGCCTGCAGCCTGAAGATGCTGCA
ACTTATTACTGTCAG

Marmoset nucleotide sequence 10 (SEQ ID No:23)
GACATCCAGATGACCCAGTCTCCATCTTCCCTGACTGCATCTGTAGGAGGCAAAGTCACCATC
ACTTGCCGGGCGAGTCAGGACATTAACAAGTGGTTAGCCTGGTATCAGCAGAAACCAGGGACA
GTCCTTAAGCCCCTGATCTATGAGGCATCCAAATTGCAAAGTGGGGTCCCATCAAGGTTCAGC
GGCAGTGGATCTGGGACATATTTTACTCTCACCATCAGCAGCCTGCAGCCTGAAGATGCTGCA
ACTTATTACTGTCAG

Marmoset nucleotide sequence 11 (SEQ ID No:24)
GACATCCAGATGACCCAGTCTCCATCTTCCCTGACTGCATCTGTAGGAGGCAAAGTCACCATC
ACTTGCCGGGCGAGTCAGGACATTAACAAGTGGTTAGCCTGGTATCAGCAGAAACCAGGGACA
GTCCCTAAGCCCCTGATCTATGAGGCATCCAAATTGCAAAGTGGGGTCCCATTAAGGTTCAGC
GGCAGTGGATCTGGGACATATTTTACTCTCACCATCAGCAGCCTGCAGCCTGAAGATGCTGCA
ACTTATTACTGTCAG

FIGURE 2C

Marmoset amino acid sequence 1 (SEQ ID No:25)
DIQMTQSPSSLTASVGGKVTITCRASQDINKWLAWYQQKPGTVPKPLIYEASKLQSGVPSRFS
GSGSGTYFTLTISSLQPEDAATYYCQ

Marmoset amino acid sequence 2 (SEQ ID No:26)
DIQMIQSPSSLSASVGDRVTITCWASQGISHWLAWYQQKPGKAPKLLIYSASNLETGVPSRFS
GSGSRTDFTLTISSLQPEDIATYYCQ

Marmoset amino acid sequence 3 (SEQ ID No:27)
DIQMTQTPSSLSASVGDRVTITCRASQGISSWLAWYQQKPGKAPKLLIYGASNLETGVPSRFS
GSGSGTDFTLTISSLQPEDIATYYCQ

Marmoset amino acid sequence 4 (SEQ ID No:28)
DIQMIQSPSSLSASVGDRVTITCWASQGISHWLAWYQQKPGKAPKLLIYSASNLGTGVPSRFS
GSGSRTDFTLTISSLQPEDIATYYCQ

Marmoset amino acid sequence 5 (SEQ ID No:29)
DIQMTQSPSSLTASVGGKVTITCRACQDINKWLAWYQQKPGTVPKPLIYEASKLQSGVPSRFS
GSGSGTYFTLTISSLQPEDAATYYCQ

Marmoset amino acid sequence 6 (SEQ ID No:30)
DIQMTQSPSSLSASVGDRVTITCRASQGISNYLAWYQQKPGKTPRLLIYAASSLQTGIPSRFS
GSGSGTDYTLTISSLQSEDVAIYYCQ

Marmoset amino acid sequence 7 (SEQ ID No:31)
DIQMTQSPSSLTASVGGKVTITCRASQDINKWLAWYQQKPGTVPKPLIYEASKLQSGVPSRLS
GSGSGTYFTLTISSLQPEDAATYYCQ

Marmoset amino acid sequence 8 (SEQ ID No:32)
DIQMTQSPSSLTASVGGKVTITCRASQDINKWSAWYQQKPGTVPKPLIYEASKLQSGVPSRFS
GSGSGTYFTLTISSLQPEDAATYYCQ

Marmoset amino acid sequence 9 (SEQ ID No:33)
DIQMTQSPSSLTASVGGKVTVTCRASQDINKWLAWYQQKPGTVPKPLIYEASKLQSGVPSRFS
GSGSGTYFTLTISSLQPEDAATYYCQ

Marmoset amino acid sequence 10 (SEQ ID No:34)
DIQMTQSPSSLTASVGGKVTITCRASQDINKWLAWYQQKPGTVLKPLIYEASKLQSGVPSRFS
GSGSGTYFTLTISSLQPEDAATYYCQ

FIGURE 2D

Marmoset amino acid sequence 11 (SEQ ID No:35)
DIQMTQSPSSLTASVGGKVTITCRASQDINKWLAWYQQKPGTVPKPLIYEASKLQSGVPLRFS
GSGSGTYFTLTISSLQPEDAATYYCQ <u>Owl Monkey sequences</u>

Owl Monkey nucleotide sequence 1 (SEQ ID No:36)
GACATCCAGATGACCCAGTCTCCATCCTTCCTGTCTGCATCTGCAGGAGACAGAGTCACCATC
ACCTGCCAGGTGAGTCAGGGAATTAGCAGTGAATTACTCTGGTATCAGCAGAAACCAGGGAAA
GCCCCTATGCTCTTGATCTATGCTGCAACCAAATTGCAGTCGGGAATCCCATCTCGGTTCAGT
GGCCATGGATCTGGGACAGATTTCACTCTCACCATCAGCAGCCTGCAGCCTGATGATTTTGCT
ACTTATTACTGTCAA

Owl Monkey nucleotide sequence 2 (SEQ ID No:37)
GACATCCAGATGACCCAGTCTGCATTCTCCCTGTCTGCATCTGTAGGAGACAGAGTCACCATT
ACTTGCCAGGCGAGTCAGGGCATTACCAGTGATTTAGCCTGGTATCAGCAAAAGCCAGGGAAC
GCCTCTAAGCTCCTGATCTATGAGGCATCCAGTTTACAAAGCGAGGTCCCATCAAGGTTCAGC
GGCAGTGGATCTGGGAGAGATTTTACTCTCACCATCAGCAGCCTGCAGCCTGAAGATTTTGTA
ACTTATTACTGTCAA

Owl Monkey nucleotide sequence 3 (SEQ ID No:38)
GACATCCAGATGACCCAGACTCCATCCTCCCTGTCTGCATCTGTAGGAGACAGAGTCACCATC
ACTTGCCGGGCGAGTCAAGACATTTACAATTATTTAGCCTGGTATCAGCAGAAACCAGGGAAA
ACTCCTAGGCTCTTGATCTATGCTGCATCCAGTTTGCAAACTGGGATTCCCTCTCGGTTCAGT
GGCAGTGGATCTGGGACAGACTACACTCTCACCATCAGCAGCCTGCAGCCTGATGATTTTGCC
ACTTATTACTGTCAA

Owl Monkey nucleotide sequence 4 (SEQ ID No:39)
GACATCCAGATGACCCAGACTCCATCCTCCCTGCCTGCATCTGTAGGAGACAAAGTCACCATC
ACTTGCCGGGCAAGTCAGGGTATTAGCAGCTGGTTAGCCTGGTATCAGCAGAAACCAGGGAAA
GCCCCTAAGCTCCTGATCCATAAGGCATCAAATTTGGAAACAGGGGTCCCATCAAGGTTCAGT
GGAAGTGGATCTGGGACAGATTTTACTCTCACCATCAGCAGCCTGCAGCCTGAAGATATCGCA
ACATATTACTGTCAA

Owl Monkey nucleotide sequence 5 (SEQ ID No:40)
GACATCCAGATGACCCAGTCTCCATCTTCCCTGACTGCATCTGTAGGAGACAAAGTCACCATC
ACTTGCCGGGCAAGTCAGGGCATTAGCAATAATTTAGCCTGGTATCAGCAGAAACCAGGGAAA
GCCCCTAAGCCCCTGATCTATTATGCATCCAGTTTGCAAAGCGGGGTCCCATCAAGGTTCAGC
GGCAGTGGATCTGGGGCAGATTACACTCTCACCACCAGCAGCCTGCAGCCTGAAGATTTTGCA
ACTTATTACTGTCAA

FIGURE 2E

Owl Monkey nucleotide Sequence 6 (SEQ ID No:41)
GACAACCAGATGATCCAGTCTCCATCTTCCCTGACTGCATCTGTAGGAGACAGAGTCACCATC
ACTTGCCGAGCCAGTCAGAGTATTAGCAGCTGGTTAGCCTGGTATCAGCAGAAACCAGGGACA
GTCCCTAAGCCTCTGATCTATGACGCATCCAAATTGCTAAGTGGGGTCCCATCAAGGTTCAGT
GGCTGTGGATCTGGGACAGATTTTACTCTCACCATCAGCAGCCTGCAGCCTGAAGATTTTGCA
ACTTATTACTGTCAA

Owl Monkey amino acid sequence 1 (SEQ ID No:42)
DIQMTQSPSFLSASAGDRVTITCQVSQGISSELLWYQQKPGKAPMLLIYAATKLQSGIPSRFS
GHGSGTDFTLTISSLQPDDFATYYCQ

Owl Monkey amino acid sequence 2 (SEQ ID No:43)
DIQMTQSAFSLSASVGDRVTITCQASQGITSDLAWYQQKPGNASKLLIYEASSLQSEVPSRFS
GSGSGRDFTLTISSLQPEDFVTYYCQ

Owl Monkey amino acid sequence 3 (SEQ ID No:44)
DIQMTQTPSSLSASVGDRVTITCRASQDIYNYLAWYQQKPGKTPRLLIYAASSLQTGIPSRFS
GSGSGTDYTLTISSLQPDDFATYYCQ

Owl Monkey amino acid sequence 4 (SEQ ID No:45)
DIQMTQTPSSLPASVGDKVTITCRASQGISSWLAWYQQKPGKAPKLLIHKASNLETGVPSRFS
GSGSGTDFTLTISSLQPEDIATYYCQ

Owl Monkey amino acid sequence 5 (SEQ ID No:46)
DIQMTQSPSSLTASVGDKVTITCRASQGISNNLAWYQQKPGKAPKPLIYYASSLQSGVPSRFS
GSGSGADYTLTTSSLQPEDFATYYCQ

Owl Monkey amino acid sequence 6 (SEQ ID No:47)
DNQMIQSPSSLTASVGDRVTITCRASQSISSWLAWYQQKPGTVPKPLIYDASKLLSGVPSRFS
GCGSGTDFTLTISSLQPEDFATYYC

1     GACATCCAGATGACCCAGTCTCCATCCTCTCTGTCTGCATCTGTAGGAGACCGTGTCACCATCACTTGCCGGGCAAGTCA    80

1     CTGTAGGTCTACTGGGTCAGAGGTAGGAGAGACAGACGTAGACATCCTCTGGCACAGTGGTAGTGAACGGCCCGTTCAGT    80

S  I  D  S  Y  L  H  W  Y  Q  Q  K  P  G  K  A  P  K  L  L  I  Y  S  A  S  E

81    GAGCATTGATAGTTATTTACATTGGTACCAGCAGAAACCAGGGAAAGCCCCTAAGCTCCTGATCTATAGTGCATCCGAGT   160

81    CTCGTAACTATCAATAAATGTAACCATGGTCGTCTTTGGTCCCTTTCGGGGATTCGAGGACTAGATATCACGTAGGCTCA   160

KpnI

L  Q  S  G  V  P  S  R  F  S  G  S  G  S  G  T  D  F  T  L  T  I  S  S  L  Q  P

161   TGCAAAGTGGGGTCCCATCACGTTTCAGTGGCAGTGGATCTGGGACAGATTTCACTCTCACCATCAGCAGTCTGCAACCT   240

161   ACGTTTCACCCCAGGGTAGTGCAAAGTCACCGTCACCTAGACCCTGTCTAAAGTGAGAGTGGTAGTCGTCAGACGTTGGA   240

SanDI

E  D  F  A  T  Y  Y  C  Q  Q  V  V  W  R  P  F  T  F  G  Q  G  T  K  V  E  I  K

241   GAAGATTTTGCTACGTACTACTGTCAACAGGTTGTGTGGCGTCCTTTTACGTTCGGCCAAGGGACCAAGGTGGAAATCAA   320

241   CTTCTAAAACGATGCATGATGACAGTTGTCCAACACACCGCAGGAAAATGCAAGCCGGTTCCCTGGTTCCACCTTTAGTT   320

R

321   ACGG   324

321   TGCC   324
```

FIGURE 4A

```
                                           10        20        30        40        50        60        70        80
                                     ....|....|....|....|....|....|....|....|....|....|....|....|....|....|....|....|
Acceptor dAb sequence                GACATCCAGATGACCCAGTCTCCATCCTCTCTGTCTGCATCTGTAGGAGACCGTGTCACCATCACTTGCCGGGCAAGTCA
Owl Monkey Sequence 1                ........................TC............C.......A.A...........C....A..TG.....
Owl Genomic 1
Owl Monkey Genomic Reverse 1
Pasting Confirmation Owl Monke       ........................C...................................................
Owl Monkey Sequence 2                ...................G...T..C...................A.A........T......A...G.....
Owl Genomic 2
Owl Monkey Genomic Reverse 2
Pasting Confirmation Owl Monke       ........................C...................................................
Marmoset Sequence 1                  ........................T..C...A............G.AAA..................G.....
Marmoset Genomic 1
Marmoset Genomic Reverse 1
Pasting Confirmation Marmoset        ........................C...................................................
Marmoset Sequence 2                  ...........T............C...................A.A...............T..........
Marmoset Genomic 2
Marmoset Genomic Reverse 2
Pasting Confirmation Marmoset        ........................C...................................................

90       100       110       120       130       140       150       160
                                     ....|....|....|....|....|....|....|....|....|....|....|....|....|....|....|....|
Acceptor dAb sequence                GAGCATTGATAGTTATTTACATTGGTACCAGCAGAAACCAGGGAAAGCCCCTAAGCTCCTGATCTATAGTGCATCCGAGT
Owl Monkey Sequence 1                .G.A...AGC...G.A....TC.....T.....................T....T........GC....A..A.A.
Owl Genomic 1                                                                                       GC....A..A.A.
Owl Monkey Genomic Reverse 1                                                                         GC....A..A.A.
Pasting Confirmation Owl Monke                                                                       GC....A..A.A.
Owl Monkey Sequence 2                .G.....ACC...G.....GCC.....T.....A..G........C...T............GAG.....AGT.
Owl Genomic 2                                                                                       GAG.....AGT.
Owl Monkey Genomic Reverse 2                                                                         GAG.....AGT.
Pasting Confirmation Owl Monke                                                                       GAG.....AGT.
Marmoset Sequence 1                  .GA....A.C.AG.GG...GCC.....T...............C..T........C......GAG......A.A.
Marmoset Genomic 1                                                                                   GAG......A.A.
Marmoset Genomic Reverse 1                                                                           GAG......A.A.
Pasting Confirmation Marmoset                                                                        GAG......A.A.
Marmoset Sequence 2                  .G.T...AGCCAC.GG...GCC.....T..........................................AA.T.
Marmoset Genomic 2                                                                                   AA.T.
Marmoset Genomic Reverse 2                                                                           AA.T.
Pasting Confirmation Marmoset                                                                        AA.T.

170       180       190       200       210       220       230       240
                                     ....|....|....|....|....|....|....|....|....|....|....|....|....|....|....|....|
Acceptor dAb sequence                TGCAAAGTGGGGTCCCATCACGTTTCAGTGGCAGTGGATCTGGGACAGATTTCACTCTCACCATCAGCAGTCTGCAACCT
Owl Monkey Sequence 1                ....GTCG...AA.......T..G.........CA.....................................C.....G...
Owl Genomic 1                        ...
Owl Monkey Genomic Reverse 1         ....GTCG...............
Pasting Confirmation Owl Monke       ....GTCG...............
Owl Monkey Sequence 2                .A......C.A...........A.G.....C............G......T.................C.....G...
Owl Genomic 2                        .A.
Owl Monkey Genomic Reverse 2         .A......C...............
Pasting Confirmation Owl Monke       .A......C...............
Marmoset Sequence 1                  ..................A.G.....C..............T....T.............C.....G...
Marmoset Genomic 1                   ...
Marmoset Genomic Reverse 1
Pasting Confirmation Marmoset
Marmoset Sequence 2                  .AG...CA..........A.G......A........CA..........T.................C.....G...
Marmoset Genomic 2                   .AG
Marmoset Genomic Reverse 2           .AG...CA............"
Pasting Confirmation Marmoset        .AG...CA..............

250       260       270       280       290       300       310       320
                                     ....|....|....|....|....|....|....|....|....|....|....|....|....|....|....|....|
Acceptor dAb sequence                GAAGATTTTGCTACGTACTACTGTCAACAGGTTGTGTGGCGTCCTTTTACGTTCGGCCAAGGGACCAAGGTGGAAATCAA
Owl Monkey Sequence 1                ..T............T..T.........
Owl Genomic 1
Owl Monkey Genomic Reverse 1
Pasting Confirmation Owl Monke       ................................................................................
Owl Monkey Sequence 2                ..........TA..T..T.........
Owl Genomic 2
Owl Monkey Genomic Reverse 2
Pasting Confirmation Owl Monke       ................................................................................
Marmoset Sequence 1                  ......GC...A..T..T........G
Marmoset Genomic 1
Marmoset Genomic Reverse 1
Pasting Confirmation Marmoset        ................................................................................
Marmoset Sequence 2                  ......A....A..A..T.........
Marmoset Genomic 2
Marmoset Genomic Reverse 2
Pasting Confirmation Marmoset        ................................................................................

Acceptor dAb sequence                ACGG
Owl Monkey Sequence 1
Owl Genomic 1
Owl Monkey Genomic Reverse 1
Pasting Confirmation Owl Monke       ....
Owl Monkey Sequence 2
Owl Genomic 2
Owl Monkey Genomic Reverse 2
Pasting Confirmation Owl Monke       ....
Marmoset Sequence 1
Marmoset Genomic 1
Marmoset Genomic Reverse 1
Pasting Confirmation Marmoset        ....
Marmoset Sequence 2
Marmoset Genomic 2
Marmoset Genomic Reverse 2
Pasting Confirmation Marmoset        ....
```

FIGURE 4B

```
                                            ....|....10...|....20...|....30...|....40...|....50...|....60...|....70...|....80
Acceptor dAb sequence                       DIQMTQSPSSLSASVGDRVTITCRASQSIDSYLHWYQQKPGKAPKLLIYSASELQSGVPSRFSGSGSGTDFTLTISSLQP
Owl Monkey Sequence 1                       ........F....A.........QV..G.S.E.L..........M....A.TK....I......H..............
Owl Genomic 1                               ~~ ~~ ~~ ~~ ~~ ~~ ~~ ~~ ~~ X.................A.TK.............................
Owl Monkey Genomic Reverse 1                ~~~~~~~~~~~~~~~~~~~~~~~~~~~~~~~~~~~X...A.TK......
Pasting Confirmation Owl Monke              .................................................A.TK...........................
Owl Monkey Sequence 2                       ......AF............Q...G.T.D.A.......N.S....E..S...E..........R............
Owl Genomic 2                               ~~ ~~ ~~ ~~ ~~ ~~ ~~ ~~ ~~ X.................E..S.
Owl Monkey Genomic Reverse 2                ~~~~~~~~~~~~~~~~~~~~~~~~~~~~~~~~~~~X...E..S......
Pasting Confirmation Owl Monke              .................................................E..S.........................
Marmoset Sequence 1                         ..........T....GK........D.NKW.A.......TV..P...E..K................Y..........
Marmoset Genomic 1                          ~~ ~~ ~~ ~~ ~~ ~~ ~~ ~~ ~~ X.................E..K.
Marmoset Genomic Reverse 1                  ~~~~~~~~~~~~~~~~~~~~~~~~~~~~~~~~~~~X...E..K......
Pasting Confirmation Marmoset               .................................................E..K.
Marmoset Sequence 2                         ....I................W...G.SHW.A..................N.ET..........R............
Marmoset Genomic 2                          ~~ ~~ ~~ ~~ ~~ ~~ ~~ ~~ ~~ X....................N.
Marmoset Genomic Reverse 2                  ~~~~~~~~~~~~~~~~~~~~~~~~~~~~~~~~~~~X......N.ET....X
Pasting Confirmation Marmoset               .................................................N.ET........................

....|....90...|....100..|....
Acceptor dAb sequence                       EDFATYYCQQVVWRPFTFGQGTKVEIKR
Owl Monkey Sequence 1                       D........
Owl Genomic 1
Owl Monkey Genomic Reverse 1
Pasting Confirmation Owl Monke              ............................
Owl Monkey Sequence 2                       ...V.....
Owl Genomic 2
Owl Monkey Genomic Reverse 2
Pasting Confirmation Owl Monke              ............................
Marmoset Sequence 1                         ..A......
Marmoset Genomic 1
Marmoset Genomic Reverse 1
Pasting Confirmation Marmoset               ............................
Marmoset Sequence 2                         ..I......
Marmoset Genomic 2
Marmoset Genomic Reverse 2
Pasting Confirmation Marmoset               ............................
```

ANTI-INFLAMMATORY DAB

CROSS REFERENCE TO RELATED APPLICATIONS

This application is a National Phase filing of International Application PCT/AU2006/001940, filed Dec. 20, 2006, which claims the benefit of U.S. provisional patent application Ser. No. 60/817,272, filed Jun. 28, 2006 and Australian application AU 2005907124, filed Dec. 20, 2005, the disclosures of which are incorporated herein by reference in their entirety.

FIELD OF THE INVENTION

The invention relates to recombinant domain antibodies (dAbs) useful for human therapy. More particularly, the present invention relates to a domain antibody (dAb) which binds to human TNF-α and its use in the treatment of disorders characterised by human TNF-α activity.

BACKGROUND OF THE INVENTION

Tumor necrosis factor alpha (TNF-α) is a cytokine produced by numerous cell types, including monocytes and macrophages, that has been implicated in mediating shock and the pathophysiology of a variety of human diseases and disorders including sepsis, infections, autoimmune diseases, transplant rejection and graft-versus-host disease.

In an effort to counter the harmful effects mediated by human TNF-α, antibodies that bind to and neutralise human TNF-α have been sought as a means to inhibit TNF-α activity. Some of the earliest antibodies directed against human TNF-α were mouse monoclonal antibodies secreted from hybridoma cell lines prepared from lymphocytes harvested from mice immunized with human TNF-α. Although such antibodies were effective in binding to and neutralising human TNF-α, their use in in vivo therapy has been limited by problems associated with the administration of mouse antibodies to humans, in particular, elicitation of an unwanted immune response against the mouse antibody in a human, referred to as human anti-mouse antibody (HAMA) reactions.

In an attempt to overcome these problems, murine antihuman TNF-α antibodies have been genetically engineered to be more human-like. For example, human/mouse chimeric antibodies have been created in which antibody variable region sequences from the mouse genome are combined with antibody constant region sequences from the human genome. The chimeric antibodies exhibit the binding characteristics of the parental mouse antibody, and the effector functions associated with the human constant region. Although these chimeric antibodies have been used in human therapy, they still retain some murine sequences and therefore still may elicit anti-chimeric antibody reactions in human recipients, particularly when administered for prolonged periods thus limiting their therapeutic application.

Human monoclonal antibodies against human TNF-α have been developed using human hybridoma techniques. This approach, however, suffers from ethical, clinical and immunological limitations on immunization of human subjects.

It has been postulated that non-human primate antibodies will be tolerated in humans because they are structurally similar to human antibodies (Ehrlich P H et al., Human and primate monoclonal antibodies for in vivo therapy. Clin Chem. 34:9 pg 1681-1688 (1988)). Furthermore, because human antibodies are non-immunogenic in Rhesus monkeys (Ehrich P H et al., Rhesus monkey responses to multiple injections of human monoclonal antibodies. Hybridoma 1987; 6:151-60), it is likely that the converse is also applicable and primate antibodies will be non-immunogenic in humans.

Evolutionarily distant primates, such as New World primates, are not only sufficiently different from humans to allow antibodies against human antigens to be generated, but are sufficiently similar to humans to have antibodies similar to human antibodies so that the host does not generate an anti-antibody immune response when such primate-derived antibodies are introduced into a human. New World primates (infraorder-Platyrrhini) comprises at least 53 species commonly divided into two families, the Callithricidae and Cebidae. The Callithricidae consist of marmosets and tamarins. The Cebidae includes the squirrel monkey, titi monkey, spider monkey, woolly monkey, capuchin, night or owl monkey and the howler monkey.

Previous studies have characterised the expressed immunoglobulin heavy chain repertoire of the *Callithrix jacchus* marmoset (von Budingen H—C et al., Characterization of the expressed immunoglobulin IGHV repertoire in the New World marmoset *Callithrix jacchus*. Immunogenetics 2001; 53:557-563). Six IGHV subgroups were identified which showed a high degree of sequence similarity to their human IGHV counterparts. The framework regions were more conserved when compared to the complementarity determining regions (CDRs). The degree of similarity between *C. jacchus* and human IGHV sequences was less than between Old World primates and humans.

Domain Antibodies

Domain antibodies (dAb) are the smallest functioning binding units of antibodies and correspond to the variable regions of either the heavy ($V_H$) or light ($V_L$) chains of antibodies. Domain antibodies have a molecular weight of approximately 13 kDa, or less than one tenth the size of a full antibody.

Immunoglobulin light chains are referred to as either kappa or lambda light chains and the heavy chains as gamma, mu, delta, alpha or epsilon. The variable region gives the antibody its specificity. Within each variable region are regions of hypervariability, otherwise known as complementarity determining regions (CDRs) which are flanked by more conserved regions referred to as framework regions. Within each variable region are three CDRs and four framework regions.

In contrast to conventional antibodies, domain antibodies are well expressed in bacterial, yeast and mammalian systems. Their small size allows for higher molar quantities per gram of product, thus providing a significant increase in potency per dose. In addition, domain antibodies can be used as a building block to create therapeutic products such as multiple targeting dAbs in which a construct containing two or more variable domains bind to two or more therapeutic targets, or dAbs targeted for pulmonary or oral administration.

SUMMARY OF THE INVENTION

In a first aspect, the present invention provides a recombinant domain antibody (dAb) which binds to human TNF-α, the dAb comprising an immunoglobulin heavy or light chain variable domain, wherein said variable domain comprises at least one complementarity determining region (CDR) having a sequence derived from a New World primate wherein the CDR is selected from the group the group consisting of AAT-KLQS (SEQ ID No:1), EASSLQS (SEQ ID No:2), EASKLQS (SEQ ID No:3) and SASNLET (SEQ ID No:4).

In a second aspect, the invention provides a pharmaceutical composition comprising an effective amount of the dAb according to the first aspect of the invention, together with a pharmaceutically acceptable carrier or diluent.

In a third aspect, the present invention provides for the use of a dAb according to the first aspect of the invention in a diagnostic application for detecting human TNF-α.

In a fourth aspect, the invention provides a method for treating a disorder characterised by human TNF-α activity in a human subject, comprising administering to the subject a pharmaceutical composition according to the second aspect of the invention.

In a fifth aspect the invention provides a nucleic acid sequence encoding the dAb of the first aspect of the invention.

BRIEF DESCRIPTION OF THE FIGURES

FIG. 1 shows the amino acid (SEQ ID No:6) and nucleotide sequence (SEQ ID No:5) of the acceptor dAb.

FIG. 2 shows the nucleotide and amino acid sequences of eleven (11) marmoset and six (6) Owl monkey Vκ gene segments.

FIG. 3 shows the acceptor dAb amino acid (SEQ ID NO:6) and nucleotide sequence (both strands) (Top strand is SEQ ID NO: 5; bottom strand is SEQ ID NO:53). The restriction digest sites for Kpn I and San DI which excises a region including the CDR2 is indicated in the figure. CDR2 residues removed are indicated in underlined.

FIG. 4 shows sequence alignments showing oligonucleotides used during cloning and final sequence confirmation of the nucleotide (A) (SEQ ID Nos: 5, 36, 54-56, 37, 57-59, 14, 60-62, 15, and 63-65) and amino acid (B) (SEQ ID Nos:) 6, 42, 66-68, 43, 69-71, 25, 72-74, 26, and 75-77) sequences shown in FIG. 2.

DETAILED DESCRIPTION OF THE INVENTION

Figure 5:
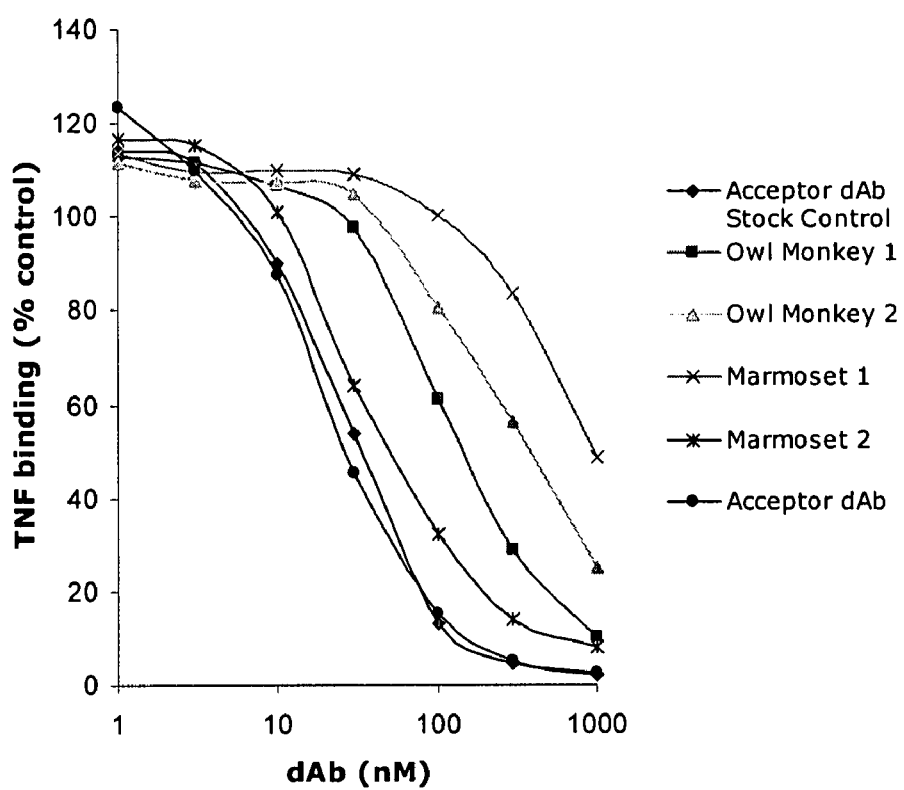
FIG. 5 demonstrates the ability of CDR2-grafted dAbs to inhibit the binding of TNF to recombinant TNF receptor. The dAbs tested were as follows: Owl Monkey 1 (CDR=AATKLQS; SEQ ID No:1), Owl Monkey 2 (CDR=EASSLQS; SEQ ID No:2), Marmoset 1 (CDR=EASKLQS; SEQ ID No:3), Marmoset 2 (CDR=SASNLET; SEQ ID No:4) and Acceptor dAb (CDR=SASELQS; SEQ ID No:49).

In a first aspect, the present invention provides a recombinant domain antibody (dAb) which binds to human TNF-α, the dAb comprising an immunoglobulin heavy or light chain variable domain, wherein said variable domain comprises at least one complementarity determining region (CDR) having a sequence derived from a New World primate wherein the CDR is selected from the group the group consisting of AATKLQS (SEQ ID No:1), EASSLQS (SEQ ID No:2), EASKLQS (SEQ ID No:3) and SASNLET (SEQ ID No:4).

Preferably, the CDR is CDR2.

In a preferred embodiment the dAb has a sequence selected from:

[Compound 145; SEQ ID No: 7]
DIQMTQSPSSLSASVGDRVTITCRASQSIDSYLHWYQQKPGKAPKLLIYS

ASNLETGVPSRFSGSGSGTDFTLTISSLQPEDFATYYCQQVVWRPFTFGQ

GTKVEIKR

[Compound 123; SEQ ID No: 8]
DIQMTQSPSSLSASVGDRVTITCRASQAIDSYLHWYQQKPGKAPKLLIYS

ASNLETGVPSRFSGSGSGTDFTLTISSLQPEDFATYYCQQVVWRPFTFGQ

GTKVEIKR

[Compound 100; SEQ ID No: 9]
DIQMTQSPSSLSASVGDRVTITCRASQSIDSYLHWYQQKPGKAPKLLIYS

ASNLETGVPSRFSGSGSGTDFTLTISSLLPEDFATYYCQQVVWRPFTFGQ

GTKVEIKR

[Compound 196; SEQ ID No: 10]
DIQMTQSPSSLSASVGDRVTITCRASQAIDSYLHWYQQKPGKAPKLLIYS

ASNLETGVPSRFSGSGSGTDFTLTISSLLPEDFATYYCQQVVWRPFTFGQ

GTKVEIKR

[Compound 134; SEQ ID No: 50]
DIQMTQSPSSLSASVGDRVTITCRASQSIDSYLHWYQQKPGKPPKLLIYS

ASNLETGVPSRFSGSGSGTDFTLTISSLQPEDFATYYCQQVVWRPFTFGQ

GTKVEIKR

[Compound 137; SEQ ID No: 51]
DIQMTQSPSSLSASVGDRVTITCRASQSIDSYLHWYQQKPGKAPKLLIYS

ASNLETGVPSRFSGRGSGTDFTLTISSLQPEDFATYYCQQVVWRPFTFGQ

GTKVEIKR

[Compound 121; SEQ ID No: 52]
DIQMTQSPSSLSASVGDRVTITCRASQSIDSYLHWYQQKPGKAPKLLIYS

ASNLETGVPSRFSGSGSGTDFTLTISSLVPEDFATYYCQQVVWRPFTFGQ

GTKVEIKR

In a further aspect the invention provides a nucleic acid sequence encoding the dAb of the first aspect of the invention.

The term "binds to" as used herein, is intended to refer to the binding of an antigen by an immunoglobulin variable region with a dissociation constant ($K_d$) of 1 μM or lower as measured by surface plasmon resonance analysis using, for example a BIAcore™ surface plasmon resonance system and BIAcore™ kinetic evaluation software (eg. version 2.1). The affinity or dissociation constant ($K_d$) for a specific binding interaction is preferably about 500 nM or lower, more preferably about 300 nM or lower and preferably at least 300 nM to 50 pM, 200 nM to 50 pM, and more preferably at least 100 nM to 50 pM, 75 nM to 50 pM, 10 nM to 50 pM.

The term "variable domain" as used herein is meant a folded polypeptide domain which comprises sequences characteristic of immunoglobulin heavy or light chain variable domains and which specifically binds an antigen. A domain antibody or dAb is equivalent to a single variable domain polypeptide.

It will be appreciated by persons skilled in the art that the remainder of the variable domain sequence may be derived from either a human, New World primate or Old World primate variable domain sequence which, because of their evolutionary association with humans, share a high degree of homology with the human sequence. Thus, for example, a CDR selected from the sequences above may be grafted into the human or primate variable region sequence to replace the wild-type CDR.

Accordingly, the invention is further based on a method for amplification of New World primate immunoglobulin variable domain genes, for example by polymerase chain reaction (PCR) from nucleic acid extracted from New World primate lymphocytes using primers specific for heavy and light chain variable domain gene families. For example, information regarding the boundaries of the variable domains of heavy and light chain genes ($V_H$ and $V_L$ respectively) can be used to design PCR primers that amplify the variable domain from a cloned heavy or light chain coding sequence encoding an antibody known to bind a given antigen. The amplified variable domain is then inserted either alone or as a fusion with another polypeptide sequence into a suitable expression vector. The expressed variable domain is then screened for high affinity binding to the desired antigen.

The repertoire of $V_H$ and $V_L$ domains can be a naturally occurring repertoire of immunoglobulin sequences or a synthetic repertoire. A naturally occurring repertoire is one prepared, for example, from immunoglobulin expressing cells harvested from one or more primates. Such repertoires can be naïve ie. prepared from newborn immunoglobulin expressing cells, or rearranged ie. prepared from, for example, adult primate B cells. If desired, clones identified from a natural repertoire, or any repertoire that bind the target antigen are then subject to mutagenesis and further screening in order to produce and select variants with improved binding characteristics.

Synthetic repertoires of single immunoglobulin variable domains are prepared by artificially introducing diversity into a cloned variable domain.

A repertoire of $V_H$ and $V_L$ domains can be screened for desired binding specificity and functional behaviour by, for example phage display. Methods for the construction of bacteriophage display libraries and lambda phage expression libraries are well known in the art. The phage display technique has been described extensively in the art and examples of methods and compounds for generating and screening such libraries and affinity maturing the products of them can be found in, for example, Barbas et al. (1991) PNAS 88:7978-7982; Clarkson et al. (1991) Nature 352:624:628; Dower et al. PCT. 91/17271, U.S. Pat. No. 5,427,908, U.S. Pat. No. 5,580,717 and EP 527,839; Fuchs et al. (1991) Bio/Technology 9:1370-1372; Garrad et al. (1991) Bio/Technology 9:1373:1377; Garrard et al. PCT WO 92/09690; Gram et al. (1992) PNAS 89:3576-3580; Griffiths et al. (1993) EMBO J. 12:725:734; Griffiths et al. U.S. Pat. No. 5,885,793 and EP 589,877; Hawkins et al. (1992) J Mol Biol 226:889-896; Hay et al. (1992) Hum Antibod Hybridomas 3:81-85; Hoogenboom et al. (1991) Nuc Acid Res 19:4133-4137; Huse et al. (1989) Science 246:1275-1281; Knappik et al. (2000) J Mol Biol 296:57-86; Knappik et al. PCT WO 97/08320; Ladner et al. U.S. Pat. No. 5,223,409, No. 5,403,484, No. 5,571,698, No. 5,837,500 and EP 436,597; McCafferty et al. (1990) Nature 348:552-554; McCafferty et al. PCT. WO 92/01047, U.S. Pat. No. 5,969,108 and EP 589,877; Salfeld et al. PCT WO 97/29131, U.S. Provisional Application No. 60/126,603; and Winter et al. PCT WO 92/20791 and EP 368,684.

Recombinant libraries expressing the repertoire of $V_H$ and $V_L$ domains can be expressed on the surface of microorganisms eg. Yeast or bacteria (see PCT publications WO99/36569 and 98/49286).

The Selective Lymphocyte Antibody Method or SLAM as it is referred to in the state of the art, is another means of generating high affinity antibodies rapidly. Unlike phage display approaches all antibodies are fully divalent. In order to generate New World primate antibodies, New World primates are immunised with a human antigen eg. a TNF-α polypeptide. Following immunisation cells are removed and selectively proliferated in individual micro wells. Supernatants are removed from wells and tested for both binding and function. Gene sequences can be recovered for subsequent manipulations eg. humanisation, Fab fragment, scFv or dAb generation. Thus another example is the derivation of the antibody or antibody species of the invention by SLAM and its derivatives (Babcock, J. S. et al 1996, Proc. Natl. Acad. Sci, USA 93; 7843-7848, U.S. Pat. No. 5,627,052 and PCT publication WO92/02551). Adaptations of SLAM, such as the use of alternatives to testing supernatants such as panning, also lie within the scope of this invention.

In one expression system the recombinant peptide/protein library is displayed on ribosomes (for examples see Roberts, R W and Szostak, J. W. 1997. Proc. Natl. Acad. Sci. USA. 94:12297-123202 and PCT Publication No. WO98/31700). Thus another example involves the generation and in vitro transcription of a DNA library (eg of antibodies or derivatives preferably prepared from immunised cells, but not so limited), translation of the library such that the protein and "immunised" mRNAs stay on the ribosome, affinity selection (eg by binding to RSP), mRNA isolation, reverse translation and subsequent amplification (eg by polymerase chain reaction or related technology). Additional rounds of selection and amplification can be coupled as necessary to affinity maturation through introduction of somatic mutation in this system or by other methods of affinity maturation as known in the state of the art.

Another example sees the application of emulsion compartmentalisation technology to the generation of the domain antibodies of the invention. In emulsion compartmentalisation, in vitro and optical sorting methods are combined with co-compartmentalisation of translated protein and its nucleotide coding sequence in aqueous phase within an oil droplet in an emulsion (see PCT publications no's WO99026711 and WO0040712). The main elements for the generation and selection of antibodies are essentially similar to the in vitro method of ribosome display.

The CDR sequences may be obtained from several sources, for example, databases e.g. The National Centre for. Biotechnology Information protein and nucleotide databases, The Kabat Database of Sequences of Proteins of Immunological Interest. Alternatively, the CDR regions can be predicted from the $V_H$ and $V_L$ domain repertoire (see for example Kabat E A and Wu T T. Attempts to locate complementarity determining residues in the variable positions of light and heavy chains. Ann. NY Acad. Sci. 190:382-93 (1971)). The CDR sequence may be a genomic DNA or a cDNA.

There are a number of ways in which a replacement CDR may be grafted into a variable domain sequence and such methods will be familiar to those skilled in the art. The preferred method of the present invention involves replacement of the CDR2 in the variable region domain via primer directed mutagenesis. This method consists of annealing a synthetic oligonucleotide encoding a desired mutations to a target region where it serves as a primer for initiation of DNA synthesis in vitro, extending the oligonucleotide by a DNA polymerase to generate a double-stranded DNA that carries the desired mutations, and ligating and cloning the sequence into an appropriate expression vector.

Preferably, the domain antibody according to the invention has low immunogenicity in humans.

By reference to the term "low immunogenicity" it is meant that the domain antibody does not raise an antibody response in a human of sufficient magnitude to reduce the effectiveness of continued administration of the antibody for a sufficient time to achieve therapeutic efficacy.

Preferably, the variable region sequence into which the CDR is grafted is the "dAb acceptor sequence" (designated Compound 128) provided in FIG. 1.

The dAb acceptor sequence consists of the amino acid sequence set forth in SEQ ID No:6:

(SEQ ID No: 6)
DIQMTQSPSSLSASVGDRVTITCRASQSIDSYLHWYQQKPGKAPKLLIYS

ASELQSGVPSRFSGSGSGTDFTLTISSLQPEDFATYYCQQVVWRPFTFGQ

GTKVEIKR.

This sequence is encoded By the nucleotide sequence set forth in SEQ ID No:5:

GAC ATC CAG ATG ACC CAG TCT CCA TCC TCT CTG TCT

GCA TCT GTA GGA GAC CGT GTC ACC ATC ACT TGC CGG

GCA AGT CAG AGC ATT GAT AGT TAT TTA CAT TGG TAC

CAG CAG AAA CCA GGG AAA GCC CCT AAG CTC CTG ATC

TAT AGT GCA TCC GAG TTG CAA AGT GGG GTC CCA TCA

CGT TTC AGT GGC AGT GGA TCT GGG ACA GAT TTC ACT

CTC ACC ATC AGC AGT CTG CAA CCT GAA GAT TTT GCT

ACG TAC TAC TGT CAA CAG GTT GTG TGG CGT CCT TTT

ACG TTC GGC CAA GGG ACC AAG GTG GAA ATC AAA CGG (SEQ ID NO: 5)

In one preferred embodiment of the present invention, a marmoset CDR sequence SASNLET (SEQ ID No:4) is grafted into the dAb acceptor sequence so as to replace the CDR2 sequence (SASELQS; SEQ ID No:49) of the dAb acceptor sequence to produce the following dAb (designated Compound 145):

Compound 145

(SEQ ID No: 7)
DIQMTQSPSSLSASVGDRVTITCRASQSIDSYLHWYQQKPGKAPKLLIYS

ASNLETGVPSRFSGSGSGTDFTLTISSLQPEDFATYYCQQVVWRPFTFGQ

GTKVEIKR

Thus, in one preferred embodiment, the dAb which binds to human TNF-α comprises the amino acid sequence of SEQ ID No:7.

It is within the scope of the present invention, that the dAb sequence may be further subject to affinity maturation in order to improve its antigen binding characteristics. This may necessitate the modification of certain amino acid residues within CDR1 and CDR3.

For example, the marmoset CDR-grafted dAb set forth in SEQ ID No:7 was affinity matured as set out in the Materials and Methods and tested for TNF-binding. In a further preferred embodiment, the dAb which binds to human TNF-α comprises the amino acid sequence of SEQ ID No:8 or SEQ ID No:9. These have been designated Compound 123 and Compound 100 respectively and their sequences are shown below:

Compound 123

(SEQ ID No: 8)
DIQMTQSPSSLSASVGDRVTITCRASQAIDSYLHWYQQKPGKAPKLLIYS

ASNLETGVPSRFSGSGSGTDFTLTISSLQPEDFATYYCQQVVWRPFTFGQ

GTKVEIKR

Compound 100

(SEQ ID No: 9)
DIQMTQSPSSLSASVGDRVTITCRASQSIDSYLHWYQQKPGKAPKLLIYS

ASNLETGVPSRFSGSGSGTDFTLTISSLLPEDFATYYCQQVVWRPFTFGQ

GTKVEIKR

In a particularly preferred embodiment, the dAb which binds to human TNF-α comprises the amino acid sequence of SEQ ID No: 10. This has been designated Compound 196 and the sequence is provided below:

Compound 196

(SEQ ID No: 10)
DIQMTQSPSSLSASVGDRVTITCRASQAIDSYLHWYQQKPGKAPKLLIYS

ASNLETGVPSRFSGSGSGTDFTLTISSLLPEDFATYYCQQVVWRPFTFGQ

GTKVEIKR

The dAb according to the invention may further comprise an immunoglobulin constant region (Fc region) connected thereto. The constant region sequence may be derived from human or primate sequences. The primate sequence may be a New World primate or an Old World primate sequence. Suitable Old World primates include chimpanzee, or other hominid ape eg. gorilla or orangutan, which because of their close phylogenetic proximity to humans, share a high degree of homology with the human constant region sequence.

The dAb (with or without the constant region connected thereto) can be derivatised or linked to another functional molecule. For example, the dAb can be functionally linked by chemical coupling, genetic fusion, noncovalent association or otherwise, to one or more other molecular entities, such as another antibody, a detectable agent, a cytotoxic agent, a pharmaceutical agent, and/or a protein or peptide that can mediate association of the antibody with another molecule (such as a streptavidin core region or a polyhistidine tag).

Useful detectable agents with which the dAb may be derivatised include fluoresceent compounds. Exemplary fluorescent detectable agents include fluorescein, fluorescein isothiocyanate, rhodamine, 5-dimethylamine-1-napthalene-sulfonyl chloride, phycoerythrin and the like. The dAb may also be derivatised with detectable enzymes such as alkaline phosphatase, horseradish peroxidase, glucose oxidase and the like. When a dAb is derivatized with a detectable enzyme, it is detected by adding additional reagents that the enzyme uses to produce a detectable reaction product. A dAb may also be derivatised with biotin, and detected through indirect measurement of avidin or streptavidin binding.

The present invention also extends to PEGylated dAbs (with or without the constant region connected thereto) which provide increased half-life and resistance to degradation without a loss in activity (eg. binding affinity) relative to non-PEGylated antibody polypeptides.

The dAb can be coupled, using methods known in the art, to polymer molecules (preferably PEG) useful for achieving the increased half-life and degradation resistance properties. Polymer moieties which can be utilised in the invention can be synthetic or naturally occurring and include, but or not limited to straight or branched chain polyalkylene, polyalkenylene or polyoxyalkylene polymers, or a branched or unbranched polysaccharide such as a homo- or heteropolysaccharide. Preferred examples of synthetic polymers which can be used in the invention include straight or branched chain poly(ethylene glycol) (PEG), poly(propylene glycol), or poly(vinyl alcohol) and derivatives or substituted forms thereof. Particularly preferred substituted polymers for linkage to dAbs include substituted PEG, including methoxy (polyethylene glycol). Naturally occurring polymer moieties which can be used in addition to or in place of PEG include lactose, amylose, dextran, or glycogen, as well as derivatives thereof which would be recognised by persons skilled in the art.

Derivatized forms of polymer molecules include, for example, derivatives which have additional moieties or reactive groups present therein to permit interaction with amino acid residues of the domain antibody polypeptides described herein. Such derivatives include N-hydroxylsuccinimide (NHS) active esters, succinimidyl propionate polymers, and sulfhydryl-selective reactive agents such as maleimide, vinyl sulfone, and thiol. PEG polymers useful in the invention can be linear molecules, or can be branched wherein multiple PEG moieties are present in a single polymer.

The reactive group (e.g., MAL, NHS, SPA, VS, or Thiol) may be attached directly to the PEG polymer or may be attached to PEG via a linker molecule.

The size of polymers useful in the invention can be in the range of between 500 Da to 60 kDa, for example, between 1000 Da and 60 kDa, 10 kDa and 60 kDa, 20 kDa and 60 kDa, 30 kDa and 60 kDa, 40 kDa and 60 kDa, and up to between 50 kDa and 60 kDa. The polymers used in the invention, particularly PEG, can be straight chain polymers or may possess a branched conformation.

The polymer (PEG) molecules useful in the invention can be attached to a domain antibody using methods which are well known in the art. The first step in the attachment of PEG or other polymer moieties to an antibody polypeptide monomer or multimer of the invention is the substitution of the hydroxyl end-groups of the PEG polymer by electrophile-containing functional groups. Particularly, PEG polymers are attached to either cysteine or lysine residues present in the domain antibody. The cysteine and lysine residues can be naturally occurring, or can be engineered into the antibody polypeptide molecule. For example, cysteine residues can be recombinantly engineered at the C-terminus of a dAb polypeptide, or residues at specific solvent accessible locations in a dAb or other antibody polypeptide can be substituted with cysteine or lysine.

The dAb according to the invention may be linked to one or more molecules which can increase its half-life in vivo. These molecules may be linked to the dAb via a linker so that they do not interfere/sterically hinder the antigen binding site. Alternatively, they may be linked to the constant region. Typically, such molecules are polypeptides which occur naturally in vivo and which resist degradation or removal by endogenous mechanisms. Molecules which increase half life may be selected from the following:

(a) proteins from the extracellular matrix, eg. collagen, laminin, integrin and fibronectin;
(b) proteins found in blood, eg. fibrin α-2 macroglobulin, serum albumin, fibrinogen A, fibrinogen B, serum amyloid protein A, heptaglobin, protein, ubiquirtin, uteroglobulin, β-2 microglobulin, plasminogen, lysozyme, cystatin C, alpha-1-antitrypsin and pancreatic kypsin inhibitor;
(c) immune serum proteins, eg. IgE, IgG, IgM;
(d) transport proteins, eg. retinol binding protein, α-1 microglobulin;
(e) defensins, eg. beta-defensin 1, Neutrophil defensins 1, 2 and 3;
(f) proteins found at the blood brain barrier or in neural tissues, eg. melanocortin receptor, myelin, ascorbate transporter;
(g) transferrin receptor specific ligand-neuropharmaceutical agent fusion proteins (see U.S. Pat. No. 5,977,307); brain capillary endothelial cell receptor, transferrin, transferrin receptor, insulin, insulin-like growth factor 1 (IGF 1) receptor, insulin-like growth factor 2 (IGF 2) receptor, insulin receptor;
(h) proteins localised to the kidney, eg. polycystin, type IV collagen, organic anion transporter K1, Heymann's antigen;
(i) proteins localised to the liver, eg. alcohol dehydrogenase, G250;
(j) blood coagulation factor X;
(k) α-1 antitrypsin;
(l) HNF Iα;
(m) proteins localised to the lung, eg. secretory component (binds IgA);
(n) proteins localised to the Heart, eg. HSP 27;
(o) proteins localised to the skin, eg, keratin;
(p) bone specific proteins, such as bone morphogenic proteins (BMPs) eg. BMP-2, -4, -5, -6, -7 (also referred to as osteogenic protein (OP-1) and -8 (OP-2);
(q) tumour specific proteins, eg. human trophoblast antigen, herceptin receptor, oestrogen receptor, cathepsins eg cathepsin B (found in liver and spleen);
(r) disease-specific proteins, eg. antigens expressed only on activated T-cells: including LAG-3 (lymphocyte activation gene); osteoprotegerin ligand (OPGL) see Nature 402, 304-309, 1999; OX40 (a member of the TNF receptor family, expressed on activated T cells and the only costimulatory T cell molecule known to be specifically up-regulated in human T cell leukaemia virus type-I (HTLV-I)-producing cells—see J. Immunol. 2000 Jul. 1; 16561):263-70; metalloproteases (associated with arthritis/cancers), including CG6512 Drosophila, human paraplegin, human FtsH, human AFG3L2, murine ftsH; angiogenic growth factors, including acidic fibroblast growth factor (FGF-1), basic fibroblast growth factor (FGF-2), vascular endothelial growth factor/vascular permeability factor (VEGF/VPF), transforming growth factor-α (TGF-α), tumor necrosis factor-alpha (TNF-α), angiogenin, interleukin-3 (IL-3), interleukin-8 (IL-8), platelet derived endothelial growth factor (PD-ECGF), placental growth factor (PlGF), midkine platelet-derived growth factor-BB (PDGF), fractalkine;
(s) stress proteins (heat shock proteins);
(t) proteins involved in Fc transport; and
(u) antibodies, fragments or derivatives directed against endogenous proteins e.g. serum albumin.

In a further embodiment of the present invention, the dAb according to the first aspect may be multimerised, as for example, hetero- or homodimers, hetero- or homotrimers, hetero- or homotetramers, or higher order hetero- or homomultimers. Multimerisation can increase the strength of antigen binding, wherein the strength of binding is related to the sum of the binding affinities of the multiple binding sites.

Thus, the invention provides a domain antibody according to the first aspect, wherein the domain antibody is linked to at least one further domain antibody. Each dAb may bind to the same or different antigens.

The dAb multimers may further comprise one or more dAbs which are linked and wherein each dAb binds to a different antigen, multi-specific ligands including so-called "dual-specific ligands". For example, the dual specific ligands may comprise a pair of $V_H$ domains or a pair of $V_L$ domains. Such dual-specific ligands are described in WO 2004/003019 (PCT/GB2003/002804) in the name of Domantis Ltd.

In a second aspect, the invention provides a pharmaceutical composition comprising an effective amount of the dAb according to the first aspect of the invention, together with a pharmaceutically acceptable carrier or diluent.

A "pharmaceutically acceptable carrier" includes any and all solvents, dispersion media, coatings, antibacterial and antifungal antifungal agents, isotonic and absorption delaying agents, and the like which are physiologically compatible. Examples of pharmaceutically acceptable carriers include one or more of water, saline, phosphate buffered saline, dextrose, glycerol, ethanol, and the like as well as combinations thereof. In many cases it will be preferable to include isotonic agents, for example, sugars, polyalcohols such as mannitol, sorbitol, or sodium chloride in the composition. Pharmaceutically acceptable substances such as wetting or minor amounts of auxiliary substances such as wetting or emulsifying agents, preservatives or buffers.

The composition may be in a variety of forms, including liquid, semi-solid and solid dosage forms, such as liquid solutions (eg injectable and infusible solutions), dispersions or suspensions, tablets, pills, powders, liposomes and suppositories. Preferably, the composition is in the form of an injectable solution for immunization. The administration may be intravenous, subcutaneous, intraperitoneal, intramuscular, transdermal, intrathecal, and intra-arterial.

Therapeutic compositions typically must be sterile and stable under the conditions of manufacture and storage. The compositions can be formulated as a solution, microemulsion, dispersion, liposome, or other ordered structure suitable to high drug concentration. Sterile injectable solutions can be prepared by incorporating the active compound (ie. dAb) into the required amount in an appropriate solvent with one or a combination of ingredients listed above, followed by filtered sterilisation.

The composition may also be formulated as a sterile powder for the preparation of sterile injectable solutions. The proper fluidity of a solution can be maintained by for example, use of a coating such as lecithin and/or surfactants.

In certain embodiments, the active compound may be prepared with a carrier that will protect the compound against rapid release, such as a controlled release formulation, including implants, transdermal patches, and microencapsulated delivery systems. Compatible polymers may be used such as ethylene vinyl acetate, polyanhydrides, polyglycolic acid, collagen, polyorthoesters and polylactic acid.

The composition may also be formulated for oral administration. In this embodiment, the dAb may be enclosed in a hard or soft shell gelatin capsule, compressed into tablets, or incorporated directly into the subject's diet.

The composition may also be formulated for rectal administration.

Supplementary active compounds can also be incorporated into the composition. The domain antibody may be co-formulated with and/or co-administered with one or more additional therapeutic agents eg. anti-inflammatory compounds, soluble TNF-α receptor or a chemical agent that inhibits human TNF-α production, or antibodies that bind other targets such as cytokines or cell surface molecules. Alternatively, it may be co-administered with a soluble immunochemical reagent such as protein A, C, G or L.

An effective amount may include a therapeutically effective amount or prophylactically effective amount of the dAb of the invention. A therapeutically effective amount refers to an amount effective at dosages and for periods of time necessary, to achieve the desired therapeutic result. A prophylactically effective amount refers to an amount effective, at dosages and for periods of time necessary, to achieve the desired prophylactic result.

In a preferred embodiment the composition is administered to mammals, preferably humans or primates.

In a third aspect, the present invention provides for the use of a dAb according to the first aspect of the invention in a diagnostic application for detecting human TNF-α.

For example, the anti-human TNF-α dAb according to the invention can be used to detect human TNF-α for example in a biological sample, such as serum or plasma using a conventional immunoassay, such as an enzyme linked immunosorbent assay (ELISA), a radioimmunoassay (RIA) or tissue immunohistochemistry. The anti-human TNF-α dAb according to the invention can be assayed in biological fluids by a competition immunoassay using recombinant human TNF-α standards labelled with a detectable substance and an unlabelled anti-human TNF-α antibody.

The anti-human TNF-α dAb according to the invention may also be used to detect TNF-α from species other than humans eg. chimpanzee, marmoset, rhesus, mouse, pig.

The anti-human TNF-α dAb according to the invention may also be used in cell culture applications where it is desired to inhibit TNF-α activity.

In a fourth aspect, the invention provides a method for treating a disorder characterised by human TNF-α activity in a human subject, comprising administering to the subject a pharmaceutical composition according to the second aspect of the invention.

A disorder characterised by human TNF-α activity is intended to include diseases and other disorders in which the presence of TNF-α in a subject suffering from the disorder has been shown to be or is suspected of being either responsible for the pathophysiology of the disorder or a factor which contributes to a worsening of the disorder. Preferably, the disorder characterised by human TNF-α activity is selected from the group consisting of inflammation, inflammatory diseases, sepsis, including septic shock, endotoxic shock, gram negative sepsis and toxic shock syndrome; autoimmune disease, including rheumatoid arthritis, rheumatoid spondylitis, osteoarthritis and gouty arthritis, allergy, multiple sclerosis, autoimmune diabetes, autoimmune uveitis and nephrotic syndrome; infectious disease, including fever and myalgias due to infection and cachexia secondary to infection; graft versus host disease; tumour growth or metastasis; pulmonary disorders including adult respiratory distress syndrome, shock lung, chronic pulmonary inflammatory disease, pulmonary sarcoidosis, pulmonary fibrosis and silicosis; inflammatory bowel disorders including Crohn's disease and ulcerative colitis; cardiac disorders; inflammatory bone disorders, hepatitis, coagulation disturbances, burns, reperfusion injury, keloid formation and scar tissue formation.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

All publications mentioned in this specification are herein incorporated by reference. Any discussion of documents, acts, materials, devices, articles or the like which has been included in the present specification is solely for the purpose of providing a context for the present invention. It is not to be taken as an admission that any or all of these matters form part of the prior art base or were common general knowledge in the field relevant to the present invention as it existed in Australia or elsewhere before the priority date of each claim of this application.

In order that the nature of the present invention may be more clearly understood, preferred forms thereof will now be described with reference to the following non-limiting examples.

Example 1

Materials and Methods

Isolation of New World Primate VL Genes

Marmoset (genus *Callithrix*, species unknown) and Owl monkey (*Aotus trivirgatus*) genomic DNA were obtained from the European Collection of Cell Cultures (ECACC), catalogue numbers 85011419 and 90110510 respectively. Marmoset DNA was derived from cell line B95-8 while Owl monkey DNA came from cell line OMK 637-69.

Degenerate primers based on human Vκ leader sequences and recombination signal sequences (RSS) were derived from Walter and Tomlinson, Antibody Engineering: A Practical Approach (1996). The primers used for amplification of germline Vκ DNA were as follows:

```
Primer VK1BL
AATCKCAGGTKCCAGATG        (SEQ ID No: 11)

Primer VK1BL35a
GTTYRGGTKKGTAACACT        (SQ ID No: 12)

Primer VK1BL35b
ATGMCTTGTWACACTGTG        (SEQ ID No: 13)
```

Genomic PCR (30 cycles) was performed using Taq polymerase with either primer pair VK1BLxVK1BL35a or VK1BLxVK1BL35b. There was overlap between the sequences cloned and the two primer sets used.

PCR products were cloned into Invitrogen's TOPO TA cloning kit (Cat No K4500-01) and sequenced with M13 forward and pUC reverse primers. Sequence was confirmed in forward and reverse directions. In order to further confirm key sequences were not subject to PCR errors, the PCR and cloning process was repeated twice for marmoset sequences. Nucleotide (SEQ ID Nos:14-24 and SEQ ID Nos:36-41) and amino acid (SEQ ID Nos:25-35 and SEQ ID Nos:42-47) are given in FIG. 2. Marmoset sequences 1, 2 and 3 were confirmed. Sequences 4, 5, 6, 7 and 8 were seen only in the initial PCR. Sequences 9, 10 and 11 were seen only in the repeat (ie second) PCR and cloning.

Oligo Synthesis and Cloning into Acceptor Sequence

Four CDR sequences, namely AATKLQS (SEQ ID No:1) from Owl monkey sequence 1 (SEQ ID No:42), EASSLQS (SEQ ID No:2) from Owl monkey sequence 2 (SEQ ID No:43), EASKLQS (SEQ ID No:3) from Marmoset sequence 1 (SEQ ID No:25), and SASNLET (SEQ ID No:4) from Marmoset sequence 2 (SEQ ID No:26), were chosen from the amino acid sequences shown in FIG. 2 as indicated. Owl Monkey sequence 5, YASSLQS (SEQ ID No:48) was found to be identical to GI6176295 an Aotus nancymaae (Ma's night monkey) cDNA sequence, all other sequences were unique.

An acceptor variable region (anti-TNF domain antibody) sequence in the expression vector (Domantis proprietary vector) was digested (25 μg) sequentially with KpnI and SanDI which excises the majority of FR2 as well as CDR2 as indicated on the restriction digest map. The vector was then gel purified to remove the excised wild-type FR2 and CDR2 sequence.

Oligo annealing was performed by incubating oligo pairs (500 pmol of each as shown in FIGS. 4A and 4B) at 95° C. for 5 minutes followed by 65° C. for 5 minutes and then allowed to reach room temperature slowly on a hot block. Overlaps were then filled in during a Klenow reaction in the presence of dNTPs.

Affinity Maturation

The marmoset CDR-grafted dAb Compound 145 (SEQ ID No:7) was affinity matured by constructing 14 separate libraries, each a diversification of the sequence of SEQ ID No:7 at a single amino acid residue. The selected residues are shown shaded below.

```
DIQMTQSPSSLSASVGDRVTITCRASQSIDSYLHWYQQKPGKAPKLL
IYSASNLETGVPSRFSGSGSGTDFTLTISSLQPEDFATYYCQQVVWR
PFTFGQGTKVEIKR
```

The selection was based upon residues in CDR1 and CDR3 that are known to be diversified in the mature human Ig repertoire, and framework residues that have been observed to produce functional proteins after mutagenesis in related dAbs. For each of the selected residues, complimentary forward and reverse PCR primer pairs were designed with NKK degeneracy, and two initial PCR reactions were performed each with a single mutagenic primer and flanking primer. After clean-up, the two PCR products were annealed and then amplified using flanking primers alone (splicing by overlap extension of PCR; Lowman H. L. & Clackson T. (eds), Phage Display: A practical approach, Oxford University Press, Oxford, UK). Clones were initially screened by ELISA using solid-phase TNF, and positive clones were sequenced. dAb protein was purified from the best clones and evaluated for potency in receptor binding assays and L929 cytotoxicity assays. Compounds 100 (SEQ ID No:9) and 123 (SEQ ID No:8) were found to have improved TNF-neutralization relative to the parent dAb, Compound 145 (SEQ ID No:7).

Combination of the affinity-enhancing substitutions of Compounds 100 (SEQ ID No:9) and 123 (SEQ ID No:8), yielded an anti-TNF dAb with further improved potency in the L929 cytotoxicity assay (Compound 196; SEQ ID No:10).

Results

Potency of Anti-TNF Dab Clones in Receptor Binding Assay (RBA) and Cytotoxocity Assay The ability of the anti-TNF dAbs to inhibit TNF binding to its receptor and to neutralize TNF-mediated cytotoxicity of L929 cells was conducted as follows:

Receptor Binding Assay dAbs diversified in the 14 selected positions were tested for the ability to inhibit the binding of TNF to recombinant TNF receptor 1 (p55). Briefly, Maxisorp plates were incubated overnight with 30 mg/ml anti-human Fc mouse monoclonal antibody (Zymed, San Francisco, USA). The wells were washed with phosphate buffered saline (PBS) containing 0.05% Tween-20 and then blocked with 1% BSA in PBS before being incubated with 100 ng/ml TNF receptor 1 Fc fusion protein (R&D Systems, Minneapolis, USA). Each dAb was mixed with TNF which was added to the washed wells at a final concentration of 10 ng/ml. TNF binding was detected with 0.2 mg/ml biotinylated anti-TNF antibody (Hy-Cult biotechnology, Uben, Netherlands) followed by 1 in 500 dilution of horse radish peroxidase labelled streptavidin (Amersham Biosciences, UK) and then incubation with TMB substrate (KPL, Gaithersburg, USA). The reaction was stopped by the addition of HCl and the absorbance was read at 450 nm. Anti-TNF dAb activity lead to a decrease in TNF binding and therefore a decrease in absorbance compared with the TNF only control (FIG. 5).

L929 Cytotoxicity Assay

Figure 6:
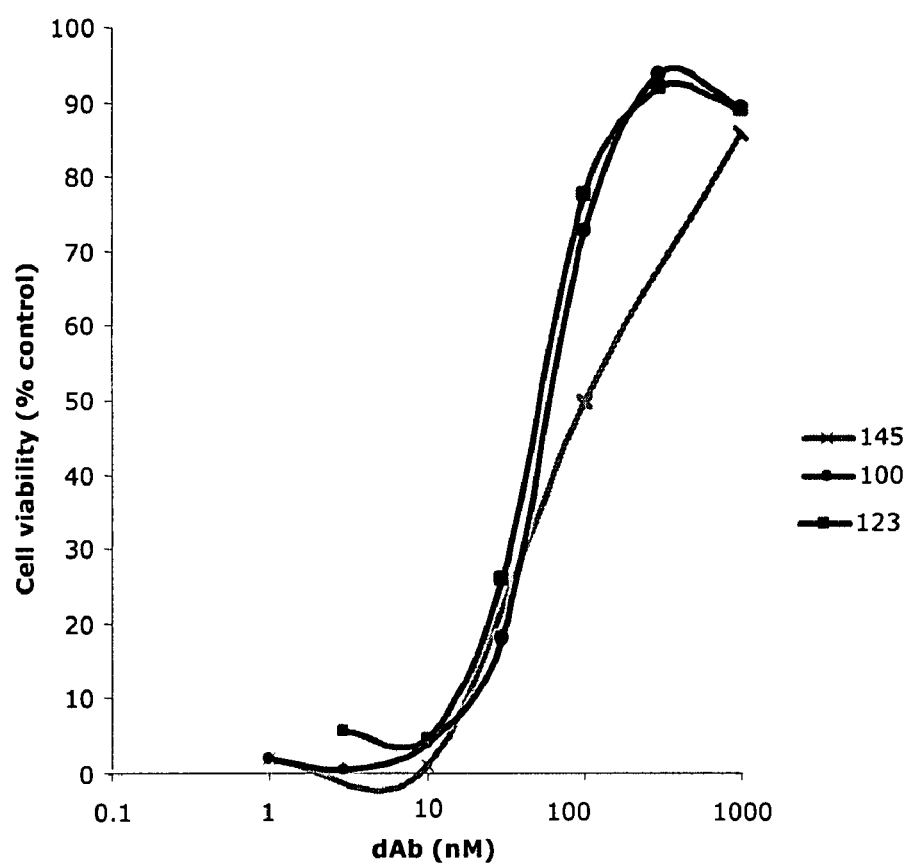
FIG. 6 demonstrates the improved ability of Compounds 100 and 123 to neutralise the cytotoxic activity of TNF on mouse L929 fibroblasts relative to acceptor dAb (Compound 145).

Anti-TNF dAbs identified by the minilibrary diversification approach, including Compounds 100 (SEQ ID No:9) and 123 (SEQ ID No:8), were also tested for the ability to neutralise the cytotoxic activity of TNF on mouse L929 fibroblasts (Evans, T. (2000) Molecular Biotechnology 15, 243-248). Briefly, L929 cells plated in microtitre plates were incubated overnight with anti-TNF dAb, 100 pg/ml TNF and 1 mg/ml actinomycin D (Sigma, Poole, UK). Cell viability was measured by reading absorbance at 490 nm following an incubation with [3-(4,5-dimethylthiazol-2-yl)-5-(3-carb-boxymethoxyphenyl)-2-(4-sulfophenyl)-2H-tetrazolium (Promega, Madison, USA). Anti-TNF dAb activity lead to a decrease in TNF cytotoxicity and therefore an increase in absorbance compared with the TNF only control. The results, in comparison with the parent dAb Compound 145 (SEQ ID No:7) are presented in FIG. 6.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

SEQUENCE LISTING

```
<160> NUMBER OF SEQ ID NOS: 77

<210> SEQ ID NO 1
<211> LENGTH: 7
<212> TYPE: PRT
<213> ORGANISM: Aotus trivirgatus

<400> SEQUENCE: 1

Ala Ala Thr Lys Leu Gln Ser
1               5

<210> SEQ ID NO 2
<211> LENGTH: 7
<212> TYPE: PRT
<213> ORGANISM: Aotus trivirgatus

<400> SEQUENCE: 2

Glu Ala Ser Ser Leu Gln Ser
1               5

<210> SEQ ID NO 3
<211> LENGTH: 7
<212> TYPE: PRT
<213> ORGANISM: Callithrix, species unknown

<400> SEQUENCE: 3

Glu Ala Ser Lys Leu Gln Ser
1               5

<210> SEQ ID NO 4
<211> LENGTH: 7
<212> TYPE: PRT
<213> ORGANISM: Callithrix, species unknown

<400> SEQUENCE: 4

Ser Ala Ser Asn Leu Glu Thr
1               5

<210> SEQ ID NO 5
<211> LENGTH: 324
<212> TYPE: DNA
<213> ORGANISM: Artificial Sequence
<220> FEATURE:
<223> OTHER INFORMATION: Synthesized contruct

<400> SEQUENCE: 5
```

```
gacatccaga tgacccagtc tccatcctct ctgtctgcat ctgtaggaga ccgtgtcacc    60
atcacttgcc gggcaagtca gagcattgat agttatttac attggtacca gcagaaacca   120
gggaaagccc ctaagctcct gatctatagt gcatccgagt tgcaaagtgg ggtcccatca   180
cgtttcagtg gcagtggatc tgggacagat ttcactctca ccatcagcag tctgcaacct   240
gaagattttg ctacgtacta ctgtcaacag gttgtgtggc gtccttttac gttcggccaa   300
gggaccaagg tggaaatcaa acgg                                         324
```

<210> SEQ ID NO 6
<211> LENGTH: 108
<212> TYPE: PRT
<213> ORGANISM: Artificial Sequence
<220> FEATURE:
<223> OTHER INFORMATION: Synthesized contruct

<400> SEQUENCE: 6

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Asp Ser Tyr
            20                  25                  30

Leu His Trp Tyr Gln Gln Lys Pro Gly Lys Ala Pro Lys Leu Leu Ile
        35                  40                  45

Tyr Ser Ala Ser Glu Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Val Val Trp Arg Pro Phe
                85                  90                  95

Thr Phe Gly Gln Gly Thr Lys Val Glu Ile Lys Arg
            100                 105

<210> SEQ ID NO 7
<211> LENGTH: 108
<212> TYPE: PRT
<213> ORGANISM: Artificial Sequence
<220> FEATURE:
<223> OTHER INFORMATION: Synthesized contruct

<400> SEQUENCE: 7

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Asp Ser Tyr
            20                  25                  30

Leu His Trp Tyr Gln Gln Lys Pro Gly Lys Ala Pro Lys Leu Leu Ile
        35                  40                  45

Tyr Ser Ala Ser Asn Leu Glu Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Val Val Trp Arg Pro Phe
                85                  90                  95

Thr Phe Gly Gln Gly Thr Lys Val Glu Ile Lys Arg
            100                 105

<210> SEQ ID NO 8
<211> LENGTH: 108
<212> TYPE: PRT
<213> ORGANISM: Artificial Sequence -continued
<220> FEATURE:
<223> OTHER INFORMATION: Synthesized contruct

<400> SEQUENCE: 8

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ala Ile Asp Ser Tyr
            20                  25                  30

Leu His Trp Tyr Gln Gln Lys Pro Gly Lys Ala Pro Lys Leu Leu Ile
        35                  40                  45

Tyr Ser Ala Ser Asn Leu Glu Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Val Val Trp Arg Pro Phe
                85                  90                  95

Thr Phe Gly Gln Gly Thr Lys Val Glu Ile Lys Arg
            100                 105

<210> SEQ ID NO 9
<211> LENGTH: 108
<212> TYPE: PRT
<213> ORGANISM: Artificial Sequence
<220> FEATURE:
<223> OTHER INFORMATION: Synthesized contruct

<400> SEQUENCE: 9

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Asp Ser Tyr
            20                  25                  30

Leu His Trp Tyr Gln Gln Lys Pro Gly Lys Ala Pro Lys Leu Leu Ile
        35                  40                  45

Tyr Ser Ala Ser Asn Leu Glu Thr Gly Val Pro Ser Arg Phe Ser Gly
    50                  55                  60

Ser Gly Ser Gly Thr Asp Phe Thr Leu Thr Ile Ser Ser Leu Leu Pro
65                  70                  75                  80

Glu Asp Phe Ala Thr Tyr Tyr Cys Gln Gln Val Val Trp Arg Pro Phe
                85                  90                  95

Thr Phe Gly Gln Gly Thr Lys Val Glu Ile Lys Arg
            100                 105

<210> SEQ ID NO 10
<211> LENGTH: 108
<212> TYPE: PRT
<213> ORGANISM: Artificial Sequence
<220> FEATURE:
<223> OTHER INFORMATION: Synthesized contruct

<400> SEQUENCE: 10

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ala Ile Asp Ser Tyr
            20                  25                  30

Leu His Trp Tyr Gln Gln Lys Pro Gly Lys Ala Pro Lys Leu Leu Ile
        35                  40                  45

Tyr Ser Ala Ser Asn Leu Glu Thr Gly Val Pro Ser Arg Phe Ser Gly
    50                  55                  60

Ser Gly Ser Gly Thr Asp Phe Thr Leu Thr Ile Ser Ser Leu Leu Pro

```
                65                  70                  75                  80
Glu Asp Phe Ala Thr Tyr Tyr Cys Gln Gln Val Val Trp Arg Pro Phe
                    85                  90                  95
Thr Phe Gly Gln Gly Thr Lys Val Glu Ile Lys Arg
            100                 105
```

<210> SEQ ID NO 11
<211> LENGTH: 18
<212> TYPE: DNA
<213> ORGANISM: Artificial Sequence
<220> FEATURE:
<223> OTHER INFORMATION: Synthesized contruct

<400> SEQUENCE: 11
aatckcaggt kccagatg                                                        18

<210> SEQ ID NO 12
<211> LENGTH: 18
<212> TYPE: DNA
<213> ORGANISM: Artificial Sequence
<220> FEATURE:
<223> OTHER INFORMATION: Synthesized contruct

<400> SEQUENCE: 12
gttyrggtkk gtaacact                                                        18

<210> SEQ ID NO 13
<211> LENGTH: 18
<212> TYPE: DNA
<213> ORGANISM: Artificial Sequence
<220> FEATURE:
<223> OTHER INFORMATION: Synthesized contruct

<400> SEQUENCE: 13
atgmcttgtw acactgtg                                                        18

<210> SEQ ID NO 14
<211> LENGTH: 267
<212> TYPE: DNA
<213> ORGANISM: Callithrix, species unknown

<400> SEQUENCE: 14
gacatccaga tgacccagtc tccatcttcc ctgactgcat ctgtaggagg caaagtcacc           60
atcacttgcc gggcgagtca ggacattaac aagtggttag cctggtatca gcagaaacca          120
gggacagtcc ctaagcccct gatctatgag gcatccaaat tgcaaagtgg ggtcccatca          180
aggttcagcg gcagtggatc tgggacatat tttactctca ccatcagcag cctgcagcct          240
gaagatgctg caacttatta ctgtcag                                             267

<210> SEQ ID NO 15
<211> LENGTH: 267
<212> TYPE: DNA
<213> ORGANISM: Callithrix, species unknown

<400> SEQUENCE: 15
gacatccaga tgatccagtc tccatcctcc ctgtctgcat ctgtaggaga cagagtcacc           60
atcacttgct gggcaagtca gggtattagc cactggttag cctggtatca gcagaaacca          120
gggaaagccc ctaagctcct gatctatagt gcatcaaatt tagaaacagg ggtcccatca          180
aggttcagtg gaagtggatc caggacagat tttactctca ccatcagcag cctgcagcct          240
gaagatattg caacatatta ctgtcaa                                             267

<210> SEQ ID NO 16
<211> LENGTH: 267
<212> TYPE: DNA
<213> ORGANISM: Callithrix, species unknown

<400> SEQUENCE: 16

| | | | | | |
|---|---|---|---|---|---|
| gacatccaga | tgacccagac | tccatcctcc | ctgtctgcat | ctgtaggaga | cagagtcacc | 60 |
| atcacttgcc | gggcaagtca | gggtattagc | agctggttag | cctggtatca | gcagaaacca | 120 |
| gggaaagccc | ctaagctcct | gatctatggg | gcatcaaatt | tggaaacagg | ggtcccatca | 180 |
| agattcagcg | gaagtggatc | tgggacagat | tttactctca | ccatcagcag | tctgcagcct | 240 |
| gaagatattg | caacatatta | ctgtcaa | | | | 267 |

<210> SEQ ID NO 17
<211> LENGTH: 267
<212> TYPE: DNA
<213> ORGANISM: Callithrix, species unknown

<400> SEQUENCE: 17

| | | | | | |
|---|---|---|---|---|---|
| gacatccaga | tgatccagtc | tccatcctcc | ctgtctgcat | ctgtaggaga | cagagtcacc | 60 |
| atcacttgct | gggcaagtca | gggtattagc | cactggttag | cctggtatca | gcagaaacca | 120 |
| gggaaagccc | ctaagctcct | gatctatagt | gcatcaaatt | taggaacagg | ggtcccatca | 180 |
| aggttcagtg | gaagtggatc | caggacagat | tttactctca | ccatcagcag | cctgcagcct | 240 |
| gaagatattg | caacatatta | ctgtcaa | | | | 267 |

<210> SEQ ID NO 18
<211> LENGTH: 267
<212> TYPE: DNA
<213> ORGANISM: Callithrix, species unknown

<400> SEQUENCE: 18

| | | | | | |
|---|---|---|---|---|---|
| gacatccaga | tgacccagtc | tccatcttcc | ctgactgcat | ctgtaggagg | caaagtcacc | 60 |
| atcacttgcc | gggcgtgtca | ggacattaac | aagtggttag | cctggtatca | gcagaaacca | 120 |
| gggacagtcc | ctaagcccct | gatctatgag | gcatccaaat | tgcaaagtgg | ggtcccatca | 180 |
| aggttcagcg | gcagtggatc | tgggacatat | tttactctca | ccatcagcag | cctgcagcct | 240 |
| gaagatgctg | caacttatta | ctgtcag | | | | 267 |

<210> SEQ ID NO 19
<211> LENGTH: 267
<212> TYPE: DNA
<213> ORGANISM: Callithrix, species unknown

<400> SEQUENCE: 19

| | | | | | |
|---|---|---|---|---|---|
| gacatccaga | tgacccagtc | tccatcctcc | ctgtctgcat | ctgtaggaga | cagagttacc | 60 |
| atcacttgcc | gggcgagtca | ggcattagt | aattatttag | cctggtatca | gcagaaacca | 120 |
| gggaaaactc | ctaggctcct | gatctatgct | gcatccagtt | tacaaactgg | gattccctct | 180 |
| cggttcagcg | gcagtggatc | tgggacagac | tacactctca | ccatcagcag | cctgcagtct | 240 |
| gaagatgttg | caatttatta | ctgtcaa | | | | 267 |

<210> SEQ ID NO 20
<211> LENGTH: 267
<212> TYPE: DNA
<213> ORGANISM: Callithrix, species unknown

<400> SEQUENCE: 20

```
gacatccaga tgacccagtc tccatcttcc ctgactgcat ctgtaggagg caaagtcacc    60
atcacttgcc gggcgagtca ggacattaac aagtggttag cctggtatca gcagaaacca   120
gggacagtcc ctaagcccct gatctatgag gcatccaaat tgcaaagtgg ggtcccatca   180
aggctcagcg gcagtggatc tgggacatat ttcactctca ccatcagcag cctgcagcct   240
gaagatgctg caacttatta ctgtcag                                       267

<210> SEQ ID NO 21
<211> LENGTH: 267
<212> TYPE: DNA
<213> ORGANISM: Callithrix, species unknown

<400> SEQUENCE: 21
gacatccaga tgacccagtc tccatcttcc ctgactgcat ctgtaggagg caaagtcacc    60
atcacttgcc gggcgagtca ggacattaac aagtggtcag cctggtatca gcagaaacca   120
gggacagtcc ctaagcccct gatctatgag gcatccaaat tgcaaagtgg ggtcccatca   180
aggttcagcg gcagtggatc tgggacatat tttactctca ccatcagcag cctgcagcct   240
gaagatgctg caacttatta ctgtcag                                       267

<210> SEQ ID NO 22
<211> LENGTH: 267
<212> TYPE: DNA
<213> ORGANISM: Callithrix, species unknown

<400> SEQUENCE: 22
gacatccaga tgacccagtc tccatcttcc ctgactgcat ctgtaggagg caaagtcacc    60
gtcacttgcc gggcgagtca ggacattaac aagtggttag cctggtatca gcagaaacca   120
gggacagtcc ctaagcccct gatctatgag gcatccaaat tgcaaagtgg ggtcccatca   180
aggttcagcg gcagtggatc tgggacatat tttactctca ccatcagcag cctgcagcct   240
gaagatgctg caacttatta ctgtcag                                       267

<210> SEQ ID NO 23
<211> LENGTH: 267
<212> TYPE: DNA
<213> ORGANISM: Callithrix, species unknown

<400> SEQUENCE: 23
gacatccaga tgacccagtc tccatcttcc ctgactgcat ctgtaggagg caaagtcacc    60
atcacttgcc gggcgagtca ggacattaac aagtggttag cctggtatca gcagaaacca   120
gggacagtcc ttaagcccct gatctatgag gcatccaaat tgcaaagtgg ggtcccatca   180
aggttcagcg gcagtggatc tgggacatat tttactctca ccatcagcag cctgcagcct   240
gaagatgctg caacttatta ctgtcag                                       267

<210> SEQ ID NO 24
<211> LENGTH: 267
<212> TYPE: DNA
<213> ORGANISM: Callithrix, species unknown

<400> SEQUENCE: 24
gacatccaga tgacccagtc tccatcttcc ctgactgcat ctgtaggagg caaagtcacc    60
atcacttgcc gggcgagtca ggacattaac aagtggttag cctggtatca gcagaaacca   120
gggacagtcc ctaagcccct gatctatgag gcatccaaat tgcaaagtgg ggtcccatta   180
aggttcagcg gcagtggatc tgggacatat tttactctca ccatcagcag cctgcagcct   240
```
gaagatgctg caacttatta ctgtcag 267

<210> SEQ ID NO 25
<211> LENGTH: 89
<212> TYPE: PRT
<213> ORGANISM: Callithrix, species unknown

<400> SEQUENCE: 25

Asp Ile Gln Met Thr Gln Ser Pro Ser Ser Leu Thr Ala Ser Val Gly
1               5                   10                  15

Gly Lys Val Thr Ile Thr Cys Arg Ala Ser Gln Asp Ile Asn Lys Trp
            20                  25                  30

Leu Ala Trp Tyr Gln Gln Lys Pro Gly Thr Val Pro Lys Pro Leu Ile
        35                  40                  45

Tyr Glu Ala Ser Lys Leu Gln Ser Gly Val Pro Ser Arg Phe Ser Gly
    50                  55                  60

Ser Gly Ser Gly Thr Tyr Phe Thr Leu Thr Ile Ser Ser Leu Gln Pro
65                  70                  75                  80

Glu Asp Ala Ala Thr Tyr Tyr Cys Gln
                85

<210> SEQ ID NO 26
<211> LENGTH: 89
<212> TYPE: PRT
<213> ORGANISM: Callithrix, species unknown

<400> SEQUENCE: 26

Asp Ile Gln Met Ile Gln Ser Pro Ser Ser Leu Ser Ala Ser Val Gly
1               5                   10                  15

Asp Arg Val Thr Ile Thr Cys Trp Ala Ser Gln Gly Ile Ser His Trp
            20                  25                  30

Leu Ala Trp Tyr Gln Gln Lys Pro Gly Lys Ala Pro Lys Leu Leu Ile
        35                  40                  45

Tyr Ser Ala Ser Asn Leu Glu Thr Gly Val Pro Ser Arg Phe Ser Gly
    50                  55                  60

Ser Gly Ser Arg Thr Asp Phe Thr Leu Thr Ile Ser Ser Leu Gln Pro
65                  70                  75                  80

Glu Asp Ile Ala Thr Tyr Tyr Cys Gln
                85

<210> SEQ ID NO 27
<211> LENGTH: 89
<212> TYPE: PRT
<213> ORGANISM: Callithrix, species unknown

<400> SEQUENCE: 27

Asp Ile Gln Met Thr Gln Thr Pro Ser Ser Leu Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Gly Lys Ala Pro Lys Leu Leu Ile
        35                  40                  45

Tyr Gly Ala Ser Asn Leu Glu Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Ile Ala Thr Tyr Tyr Cys Gln
                85

```
<210> SEQ ID NO 28
<211> LENGTH: 89
<212> TYPE: PRT
<213> ORGANISM: Callithrix, species unknown

<400> SEQUENCE: 28

Asp Ile Gln Met Ile Gln Ser Pro Ser Ser Leu Ser Ala Ser Val Gly
 1               5                  10                  15

Asp Arg Val Thr Ile Thr Cys Trp Ala Ser Gln Gly Ile Ser His Trp
            20                  25                  30

Leu Ala Trp Tyr Gln Gln Lys Pro Gly Lys Ala Pro Lys Leu Leu Ile
        35                  40                  45

Tyr Ser Ala Ser Asn Leu Gly Thr Gly Val Pro Ser Arg Phe Ser Gly
50                  55                  60

Ser Gly Ser Arg Thr Asp Phe Thr Leu Thr Ile Ser Ser Leu Gln Pro
65                  70                  75                  80

Glu Asp Ile Ala Thr Tyr Tyr Cys Gln
                85

<210> SEQ ID NO 29
<211> LENGTH: 89
<212> TYPE: PRT
<213> ORGANISM: Callithrix, species unknown

<400> SEQUENCE: 29

Asp Ile Gln Met Thr Gln Ser Pro Ser Ser Leu Thr Ala Ser Val Gly
 1               5                  10                  15

Gly Lys Val Thr Ile Thr Cys Arg Ala Cys Gln Asp Ile Asn Lys Trp
            20                  25                  30

Leu Ala Trp Tyr Gln Gln Lys Pro Gly Thr Val Pro Lys Pro Leu Ile
        35                  40                  45

Tyr Glu Ala Ser Lys Leu Gln Ser Gly Val Pro Ser Arg Phe Ser Gly
50                  55                  60

Ser Gly Ser Gly Thr Tyr Phe Thr Leu Thr Ile Ser Ser Leu Gln Pro
65                  70                  75                  80

Glu Asp Ala Ala Thr Tyr Tyr Cys Gln
                85

<210> SEQ ID NO 30
<211> LENGTH: 89
<212> TYPE: PRT
<213> ORGANISM: Callithrix, species unknown

<400> SEQUENCE: 30

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Gly Ile Ser Asn Tyr
            20                  25                  30

Leu Ala Trp Tyr Gln Gln Lys Pro Gly Lys Thr Pro Arg Leu Leu Ile
        35                  40                  45

Tyr Ala Ala Ser Ser Leu Gln Thr Gly Ile Pro Ser Arg Phe Ser Gly
50                  55                  60

Ser Gly Ser Gly Thr Asp Tyr Thr Leu Thr Ile Ser Ser Leu Gln Ser
65                  70                  75                  80

Glu Asp Val Ala Ile Tyr Tyr Cys Gln
                85

<210> SEQ ID NO 31
```

```
<211> LENGTH: 89
<212> TYPE: PRT
<213> ORGANISM: Callithrix, species unknown

<400> SEQUENCE: 31

Asp Ile Gln Met Thr Gln Ser Pro Ser Ser Leu Thr Ala Ser Val Gly
1               5                   10                  15

Gly Lys Val Thr Ile Thr Cys Arg Ala Ser Gln Asp Ile Asn Lys Trp
            20                  25                  30

Leu Ala Trp Tyr Gln Gln Lys Pro Gly Thr Val Pro Lys Pro Leu Ile
        35                  40                  45

Tyr Glu Ala Ser Lys Leu Gln Ser Gly Val Pro Ser Arg Leu Ser Gly
50                  55                  60

Ser Gly Ser Gly Thr Tyr Phe Thr Leu Thr Ile Ser Ser Leu Gln Pro
65                  70                  75                  80

Glu Asp Ala Ala Thr Tyr Tyr Cys Gln
                85

<210> SEQ ID NO 32
<211> LENGTH: 89
<212> TYPE: PRT
<213> ORGANISM: Callithrix, species unknown

<400> SEQUENCE: 32

Asp Ile Gln Met Thr Gln Ser Pro Ser Ser Leu Thr Ala Ser Val Gly
1               5                   10                  15

Gly Lys Val Thr Ile Thr Cys Arg Ala Ser Gln Asp Ile Asn Lys Trp
            20                  25                  30

Ser Ala Trp Tyr Gln Gln Lys Pro Gly Thr Val Pro Lys Pro Leu Ile
        35                  40                  45

Tyr Glu Ala Ser Lys Leu Gln Ser Gly Val Pro Ser Arg Phe Ser Gly
50                  55                  60

Ser Gly Ser Gly Thr Tyr Phe Thr Leu Thr Ile Ser Ser Leu Gln Pro
65                  70                  75                  80

Glu Asp Ala Ala Thr Tyr Tyr Cys Gln
                85

<210> SEQ ID NO 33
<211> LENGTH: 89
<212> TYPE: PRT
<213> ORGANISM: Callithrix, species unknown

<400> SEQUENCE: 33

Asp Ile Gln Met Thr Gln Ser Pro Ser Ser Leu Thr Ala Ser Val Gly
1               5                   10                  15

Gly Lys Val Thr Val Thr Cys Arg Ala Ser Gln Asp Ile Asn Lys Trp
            20                  25                  30

Leu Ala Trp Tyr Gln Gln Lys Pro Gly Thr Val Pro Lys Pro Leu Ile
        35                  40                  45

Tyr Glu Ala Ser Lys Leu Gln Ser Gly Val Pro Ser Arg Phe Ser Gly
50                  55                  60

Ser Gly Ser Gly Thr Tyr Phe Thr Leu Thr Ile Ser Ser Leu Gln Pro
65                  70                  75                  80

Glu Asp Ala Ala Thr Tyr Tyr Cys Gln
                85

<210> SEQ ID NO 34
<211> LENGTH: 89
<212> TYPE: PRT
```

<210> SEQ ID NO 34
<213> ORGANISM: Callithrix, species unknown

<400> SEQUENCE: 34

```
Asp Ile Gln Met Thr Gln Ser Pro Ser Ser Leu Thr Ala Ser Val Gly
 1               5                  10                  15
Gly Lys Val Thr Ile Thr Cys Arg Ala Ser Gln Asp Ile Asn Lys Trp
            20                  25                  30
Leu Ala Trp Tyr Gln Gln Lys Pro Gly Thr Val Leu Lys Pro Leu Ile
        35                  40                  45
Tyr Glu Ala Ser Lys Leu Gln Ser Gly Val Pro Ser Arg Phe Ser Gly
    50                  55                  60
Ser Gly Ser Gly Thr Tyr Phe Thr Leu Thr Ile Ser Ser Leu Gln Pro
65                  70                  75                  80
Glu Asp Ala Ala Thr Tyr Tyr Cys Gln
                85
```

<210> SEQ ID NO 35
<211> LENGTH: 89
<212> TYPE: PRT
<213> ORGANISM: Callithrix, species unknown

<400> SEQUENCE: 35

```
Asp Ile Gln Met Thr Gln Ser Pro Ser Ser Leu Thr Ala Ser Val Gly
 1               5                  10                  15
Gly Lys Val Thr Ile Thr Cys Arg Ala Ser Gln Asp Ile Asn Lys Trp
            20                  25                  30
Leu Ala Trp Tyr Gln Gln Lys Pro Gly Thr Val Pro Lys Pro Leu Ile
        35                  40                  45
Tyr Glu Ala Ser Lys Leu Gln Ser Gly Val Pro Leu Arg Phe Ser Gly
    50                  55                  60
Ser Gly Ser Gly Thr Tyr Phe Thr Leu Thr Ile Ser Ser Leu Gln Pro
65                  70                  75                  80
Glu Asp Ala Ala Thr Tyr Tyr Cys Gln
                85
```

<210> SEQ ID NO 36
<211> LENGTH: 267
<212> TYPE: DNA
<213> ORGANISM: Aotus trivirgatus

<400> SEQUENCE: 36

```
gacatccaga tgacccagtc tccatccttc ctgtctgcat ctgcaggaga cagagtcacc    60
atcacctgcc aggtgagtca gggaattagc agtgaattac tctggtatca gcagaaacca   120
gggaaagccc ctatgctctt gatctatgct gcaaccaaat tgcagtcggg aatcccatct   180
cggttcagtg ccatggatc tgggacagat ttcactctca ccatcagcag cctgcagcct   240
gatgattttg ctacttatta ctgtcaa                                       267
```

<210> SEQ ID NO 37
<211> LENGTH: 267
<212> TYPE: DNA
<213> ORGANISM: Aotus trivirgatus

<400> SEQUENCE: 37

```
gacatccaga tgacccagtc tgcattctcc ctgtctgcat ctgtaggaga cagagtcacc    60
attacttgcc aggcgagtca gggcattacc agtgatttag cctggtatca gcaaaagcca   120
gggaacgcct ctaagctcct gatctatgag gcatccagtt tacaaagcga ggtcccatca   180
```

```
aggttcagcg gcagtggatc tgggagagat tttactctca ccatcagcag cctgcagcct    240
gaagattttg taacttatta ctgtcaa                                        267

<210> SEQ ID NO 38
<211> LENGTH: 267
<212> TYPE: DNA
<213> ORGANISM: Aotus trivirgatus

<400> SEQUENCE: 38
gacatccaga tgacccagac tccatcctcc ctgtctgcat ctgtaggaga cagagtcacc    60
atcacttgcc gggcgagtca agacatttac aattatttag cctggtatca gcagaaacca    120
gggaaaactc ctaggctctt gatctatgct gcatccagtt tgcaaactgg gattccctct    180
cggttcagtg gcagtggatc tgggacagac tacactctca ccatcagcag cctgcagcct    240
gatgattttg ccacttatta ctgtcaa                                        267

<210> SEQ ID NO 39
<211> LENGTH: 267
<212> TYPE: DNA
<213> ORGANISM: Aotus trivirgatus

<400> SEQUENCE: 39
gacatccaga tgacccagac tccatcctcc ctgcctgcat ctgtaggaga caaagtcacc    60
atcacttgcc gggcaagtca gggtattagc agctggttag cctggtatca gcagaaacca    120
gggaaagccc ctaagctcct gatccataag gcatcaaatt tggaaacagg gtcccatca     180 aggttcagtg gaagtggatc tgggacagat tttactctca ccatcagcag cctgcagcct    240
gaagatatcg caacatatta ctgtcaa                                        267

<210> SEQ ID NO 40
<211> LENGTH: 267
<212> TYPE: DNA
<213> ORGANISM: Aotus trivirgatus

<400> SEQUENCE: 40
gacatccaga tgacccagtc tccatcttcc ctgactgcat ctgtaggaga caaagtcacc    60
atcacttgcc gggcaagtca gggcattagc aataatttag cctggtatca gcagaaacca    120
gggaaagccc ctaagcccct gatctattat gcatccagtt tgcaaagcgg ggtcccatca    180
aggttcagcg gcagtggatc tggggcagat tacactctca ccaccagcag cctgcagcct    240
gaagattttg caacttatta ctgtcaa                                        267

<210> SEQ ID NO 41
<211> LENGTH: 267
<212> TYPE: DNA
<213> ORGANISM: Aotus trivirgatus

<400> SEQUENCE: 41
gacaaccaga tgatccagtc tccatcttcc ctgactgcat ctgtaggaga cagagtcacc    60
atcacttgcc gagccagtca gagtattagc agctggttag cctggtatca gcagaaacca    120
gggacagtcc ctaagcctct gatctatgac gcatccaaat tgctaagtgg ggtcccatca    180
aggttcagtg gctgtggatc tgggacagat tttactctca ccatcagcag cctgcagcct    240
gaagattttg caacttatta ctgtcaa                                        267

<210> SEQ ID NO 42
<211> LENGTH: 89
<212> TYPE: PRT
```

<213> ORGANISM: Aotus trivirgatus

<400> SEQUENCE: 42

Asp Ile Gln Met Thr Gln Ser Pro Ser Phe Leu Ser Ala Ser Ala Gly
1               5                   10                  15

Asp Arg Val Thr Ile Thr Cys Gln Val Ser Gln Gly Ile Ser Ser Glu
            20                  25                  30

Leu Leu Trp Tyr Gln Gln Lys Pro Gly Lys Ala Pro Met Leu Leu Ile
        35                  40                  45

Tyr Ala Ala Thr Lys Leu Gln Ser Gly Ile Pro Ser Arg Phe Ser Gly
    50                  55                  60

His Gly Ser Gly Thr Asp Phe Thr Leu Thr Ile Ser Ser Leu Gln Pro
65                  70                  75                  80

Asp Asp Phe Ala Thr Tyr Tyr Cys Gln
                85

<210> SEQ ID NO 43
<211> LENGTH: 89
<212> TYPE: PRT
<213> ORGANISM: Aotus trivirgatus

<400> SEQUENCE: 43

Asp Ile Gln Met Thr Gln Ser Ala Phe Ser Leu Ser Ala Ser Val Gly
1               5                   10                  15

Asp Arg Val Thr Ile Thr Cys Gln Ala Ser Gln Gly Ile Thr Ser Asp
            20                  25                  30

Leu Ala Trp Tyr Gln Gln Lys Pro Gly Asn Ala Ser Lys Leu Leu Ile
        35                  40                  45

Tyr Glu Ala Ser Ser Leu Gln Ser Glu Val Pro Ser Arg Phe Ser Gly
    50                  55                  60

Ser Gly Ser Gly Arg Asp Phe Thr Leu Thr Ile Ser Ser Leu Gln Pro
65                  70                  75                  80

Glu Asp Phe Val Thr Tyr Tyr Cys Gln
                85

<210> SEQ ID NO 44
<211> LENGTH: 89
<212> TYPE: PRT
<213> ORGANISM: Aotus trivirgatus

<400> SEQUENCE: 44

Asp Ile Gln Met Thr Gln Thr Pro Ser Ser Leu Ser Ala Ser Val Gly
1               5                   10                  15

Asp Arg Val Thr Ile Thr Cys Arg Ala Ser Gln Asp Ile Tyr Asn Tyr
            20                  25                  30

Leu Ala Trp Tyr Gln Gln Lys Pro Gly Lys Thr Pro Arg Leu Leu Ile
        35                  40                  45

Tyr Ala Ala Ser Ser Leu Gln Thr Gly Ile Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Asp Asp Phe Ala Thr Tyr Tyr Cys Gln
                85

<210> SEQ ID NO 45
<211> LENGTH: 89
<212> TYPE: PRT
<213> ORGANISM: Aotus trivirgatus

```
<400> SEQUENCE: 45

Asp Ile Gln Met Thr Gln Thr Pro Ser Ser Leu Pro Ala Ser Val Gly
 1               5                  10                  15

Asp Lys Val Thr Ile Thr Cys Arg Ala Ser Gln Gly Ile Ser Ser Trp
            20                  25                  30

Leu Ala Trp Tyr Gln Gln Lys Pro Gly Lys Ala Pro Lys Leu Leu Ile
        35                  40                  45

His Lys Ala Ser Asn Leu Glu Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Ile Ala Thr Tyr Tyr Cys Gln
                85

<210> SEQ ID NO 46
<211> LENGTH: 89
<212> TYPE: PRT
<213> ORGANISM: Aotus trivirgatus

<400> SEQUENCE: 46

Asp Ile Gln Met Thr Gln Ser Pro Ser Ser Leu Thr Ala Ser Val Gly
 1               5                  10                  15

Asp Lys Val Thr Ile Thr Cys Arg Ala Ser Gln Gly Ile Ser Asn Asn
            20                  25                  30

Leu Ala Trp Tyr Gln Gln Lys Pro Gly Lys Ala Pro Lys Pro Leu Ile
        35                  40                  45

Tyr Tyr Ala Ser Ser Leu Gln Ser Gly Val Pro Ser Arg Phe Ser Gly
    50                  55                  60

Ser Gly Ser Gly Ala Asp Tyr Thr Leu Thr Thr Ser Ser Leu Gln Pro
65                  70                  75                  80

Glu Asp Phe Ala Thr Tyr Tyr Cys Gln
                85

<210> SEQ ID NO 47
<211> LENGTH: 89
<212> TYPE: PRT
<213> ORGANISM: Aotus trivirgatus

<400> SEQUENCE: 47

Asp Asn Gln Met Ile Gln Ser Pro Ser Ser Leu Thr Ala Ser Val Gly
 1               5                  10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Thr Val Pro Lys Pro Leu Ile
        35                  40                  45

Tyr Asp Ala Ser Lys Leu Leu Ser Gly Val Pro Ser Arg Phe Ser Gly
    50                  55                  60

Cys Gly Ser Gly Thr Asp Phe Thr Leu Thr Ile Ser Ser Leu Gln Pro
65                  70                  75                  80

Glu Asp Phe Ala Thr Tyr Tyr Cys Gln
                85

<210> SEQ ID NO 48
<211> LENGTH: 7
<212> TYPE: PRT
<213> ORGANISM: Aotus trivirgatus

<400> SEQUENCE: 48
```

```
Tyr Ala Ser Ser Leu Gln Ser
 1               5
```

<210> SEQ ID NO 49
<211> LENGTH: 7
<212> TYPE: PRT
<213> ORGANISM: Artificial Sequence
<220> FEATURE:
<223> OTHER INFORMATION: Synthesized contruct

<400> SEQUENCE: 49

```
Ser Ala Ser Glu Leu Gln Ser
 1               5
```

<210> SEQ ID NO 50
<211> LENGTH: 108
<212> TYPE: PRT
<213> ORGANISM: Artificial Sequence
<220> FEATURE:
<223> OTHER INFORMATION: Synthesized contruct

<400> SEQUENCE: 50

```
Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Ser Ile Asp Ser Tyr
                20                  25                  30

Leu His Trp Tyr Gln Gln Lys Pro Gly Lys Pro Lys Leu Leu Ile
            35                  40                  45

Tyr Ser Ala Ser Asn Leu Glu Thr Gly Val Pro Ser Arg Phe Ser Gly
     50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Val Val Trp Arg Pro Phe
                85                  90                  95

Thr Phe Gly Gln Gly Thr Lys Val Glu Ile Lys Arg
            100                 105
```

<210> SEQ ID NO 51
<211> LENGTH: 108
<212> TYPE: PRT
<213> ORGANISM: Artificial Sequence
<220> FEATURE:
<223> OTHER INFORMATION: Synthesized contruct

<400> SEQUENCE: 51

```
Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Ser Ile Asp Ser Tyr
                20                  25                  30

Leu His Trp Tyr Gln Gln Lys Pro Gly Lys Ala Pro Lys Leu Leu Ile
            35                  40                  45

Tyr Ser Ala Ser Asn Leu Glu Thr Gly Val Pro Ser Arg Phe Ser Gly
     50                  55                  60

Arg Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Val Val Trp Arg Pro Phe
                85                  90                  95

Thr Phe Gly Gln Gly Thr Lys Val Glu Ile Lys Arg
            100                 105
```

<210> SEQ ID NO 52

```
<211> LENGTH: 108
<212> TYPE: PRT
<213> ORGANISM: Artificial Sequence
<220> FEATURE:
<223> OTHER INFORMATION: Synthesized contruct

<400> SEQUENCE: 52

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Asp Ser Tyr
            20                  25                  30

Leu His Trp Tyr Gln Gln Lys Pro Gly Lys Ala Pro Lys Leu Leu Ile
        35                  40                  45

Tyr Ser Ala Ser Asn Leu Glu Thr Gly Val Pro Ser Arg Phe Ser Gly
    50                  55                  60

Ser Gly Ser Gly Thr Asp Phe Thr Leu Thr Ile Ser Ser Leu Val Pro
65                  70                  75                  80

Glu Asp Phe Ala Thr Tyr Tyr Cys Gln Gln Val Val Trp Arg Pro Phe
                85                  90                  95

Thr Phe Gly Gln Gly Thr Lys Val Glu Ile Lys Arg
            100                 105

<210> SEQ ID NO 53
<211> LENGTH: 324
<212> TYPE: DNA
<213> ORGANISM: Artificial Sequence
<220> FEATURE:
<223> OTHER INFORMATION: Synthesized contruct

<400> SEQUENCE: 53
ccgtttgatt tccaccttgg tcccttggcc gaacgtaaaa ggacgccaca caacctgttg      60
acagtagtac gtagcaaaat cttcaggttg cagactgctg atggtgagag tgaaatctgt     120
cccagatcca ctgccactga aacgtgatgg acccccactt tgcaactcgg atgcactata     180
gatcaggagc ttaggggctt tccctggttt ctgctggtac caatgtaaat aactatcaat     240
gctctgactt gcccggcaag tgatggtgac acggtctcct acagatgcag acagagagga     300
tggagactgg gtcatctgga tgtc                                            324

<210> SEQ ID NO 54
<211> LENGTH: 68
<212> TYPE: DNA
<213> ORGANISM: Aotus trivirgatus

<400> SEQUENCE: 54
tttacattgg taccagcaga aaccagggaa agcccctaag ctcctgatct atgctgcaac      60
caaattgc                                                              68

<210> SEQ ID NO 55
<211> LENGTH: 45
<212> TYPE: DNA
<213> ORGANISM: Aotus trivirgatus

<400> SEQUENCE: 55
cctgatctat gctgcaacca aattgcagtc gggggtccca tcacg                     45

<210> SEQ ID NO 56
<211> LENGTH: 324
<212> TYPE: DNA
<213> ORGANISM: Aotus trivirgatus

<400> SEQUENCE: 56
```

```
gacatccaga tgacccagtc tccatcctcc ctgtctgcat ctgtaggaga ccgtgtcacc      60
atcacttgcc gggcaagtca gagcattgat agttatttac attggtacca gcagaaacca     120
gggaaagccc ctaagctcct gatctatgct gcaaccaaat tgcagtcggg ggtcccatca     180
cgtttcagtg gcagtggatc tgggacagat ttcactctca ccatcagcag tctgcaacct     240
gaagattttg ctacgtacta ctgtcaacag gttgtgtggc gtccttttac gttcggccaa     300
gggaccaagg tggaaatcaa acgg                                            324
```

<210> SEQ ID NO 57
<211> LENGTH: 68
<212> TYPE: DNA
<213> ORGANISM: Aotus trivirgatus

<400> SEQUENCE: 57

```
tttacattgg taccagcaga aaccagggaa agcccctaag ctcctgatct atgaggcatc      60
cagtttac                                                              68
```

<210> SEQ ID NO 58
<211> LENGTH: 45
<212> TYPE: DNA
<213> ORGANISM: Aotus trivirgatus

<400> SEQUENCE: 58

```
cctgatctat gaggcatcca gtttacaaag cggggtccca tcacg                     45
```

<210> SEQ ID NO 59
<211> LENGTH: 324
<212> TYPE: DNA
<213> ORGANISM: Aotus trivirgatus

<400> SEQUENCE: 59

```
gacatccaga tgacccagtc tccatcctcc ctgtctgcat ctgtaggaga ccgtgtcacc      60
atcacttgcc gggcaagtca gagcattgat agttatttac attggtacca gcagaaacca     120
gggaaagccc ctaagctcct gatctatgag catccagtt tacaaagcgg ggtcccatca     180
cgtttcagtg gcagtggatc tgggacagat ttcactctca ccatcagcag tctgcaacct     240
gaagattttg ctacgtacta ctgtcaacag gttgtgtggc gtccttttac gttcggccaa     300
gggaccaagg tggaaatcaa acgg                                            324
```

<210> SEQ ID NO 60
<211> LENGTH: 68
<212> TYPE: DNA
<213> ORGANISM: Callithrix, species unknown

<400> SEQUENCE: 60

```
tttacattgg taccagcaga aaccagggaa agcccctaag ctcctgatct atgaggcatc      60
caaattgc                                                              68
```

<210> SEQ ID NO 61
<211> LENGTH: 45
<212> TYPE: DNA
<213> ORGANISM: Callithrix, species unknown

<400> SEQUENCE: 61

```
cctgatctat gaggcatcca aattgcaaag tggggtccca tcacg                     45
```

<210> SEQ ID NO 62
<211> LENGTH: 324

```
<212> TYPE: DNA
<213> ORGANISM: Callithrix, species unknown

<400> SEQUENCE: 62
gacatccaga tgacccagtc tccatcctcc ctgtctgcat ctgtaggaga ccgtgtcacc    60
atcacttgcc gggcaagtca gagcattgat agttatttac attggtacca gcagaaacca   120
gggaaagccc ctaagctcct gatctatgag gcatccaaat tgcaaagtgg ggtcccatca   180
cgtttcagtg gcagtggatc tgggacagat ttcactctca ccatcagcag tctgcaacct   240
gaagattttg ctacgtacta ctgtcaacag gttgtgtggc gtccttttac gttcggccaa   300
gggaccaagg tggaaatcaa acgg                                          324

<210> SEQ ID NO 63
<211> LENGTH: 68
<212> TYPE: DNA
<213> ORGANISM: Callithrix, species unknown

<400> SEQUENCE: 63
tttacattgg taccagcaga aaccagggaa agcccctaag ctcctgatct atagtgcatc    60
aaatttag                                                             68

<210> SEQ ID NO 64
<211> LENGTH: 45
<212> TYPE: DNA
<213> ORGANISM: Callithrix, species unknown

<400> SEQUENCE: 64
cctgatctat agtgcatcaa atttagaaac aggggtccca tcacg                    45

<210> SEQ ID NO 65
<211> LENGTH: 324
<212> TYPE: DNA
<213> ORGANISM: Callithrix, species unknown

<400> SEQUENCE: 65
gacatccaga tgacccagtc tccatcctcc ctgtctgcat ctgtaggaga ccgtgtcacc    60
atcacttgcc gggcaagtca gagcattgat agttatttac attggtacca gcagaaacca   120
gggaaagccc ctaagctcct gatctatagt gcatcaaatt tagaaacagg ggtcccatca   180
cgtttcagtg gcagtggatc tgggacagat ttcactctca ccatcagcag tctgcaacct   240
gaagattttg ctacgtacta ctgtcaacag gttgtgtggc gtccttttac gttcggccaa   300
gggaccaagg tggaaatcaa acgg                                          324

<210> SEQ ID NO 66
<211> LENGTH: 23
<212> TYPE: PRT
<213> ORGANISM: Aotus trivirgatus
<220> FEATURE:
<221> NAME/KEY: VARIANT
<222> LOCATION: 1
<223> OTHER INFORMATION: Xaa = Any Amino Acid

<400> SEQUENCE: 66

Xaa Leu His Trp Tyr Gln Gln Lys Pro Gly Lys Ala Pro Lys Leu Leu
1               5                   10                  15

Ile Tyr Ala Ala Thr Lys Leu
            20

<210> SEQ ID NO 67
<211> LENGTH: 15
```

```
<212> TYPE: PRT
<213> ORGANISM: Aotus trivirgatus
<220> FEATURE:
<221> NAME/KEY: VARIANT
<222> LOCATION: 1
<223> OTHER INFORMATION: Xaa = Any Amino Acid

<400> SEQUENCE: 67

Xaa Leu Ile Tyr Ala Ala Thr Lys Leu Gln Ser Gly Val Pro Ser
 1               5                  10                  15

<210> SEQ ID NO 68
<211> LENGTH: 108
<212> TYPE: PRT
<213> ORGANISM: Aotus trivirgatus

<400> SEQUENCE: 68

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Ser Ile Asp Ser Tyr
                20                  25                  30

Leu His Trp Tyr Gln Gln Lys Pro Gly Lys Ala Pro Lys Leu Leu Ile
            35                  40                  45

Tyr Ala Ala Thr Lys Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Val Val Trp Arg Pro Phe
                85                  90                  95

Thr Phe Gly Gln Gly Thr Lys Val Glu Ile Lys Arg
            100                 105

<210> SEQ ID NO 69
<211> LENGTH: 23
<212> TYPE: PRT
<213> ORGANISM: Aotus trivirgatus
<220> FEATURE:
<221> NAME/KEY: VARIANT
<222> LOCATION: 1
<223> OTHER INFORMATION: Xaa = Any Amino Acid

<400> SEQUENCE: 69

Xaa Leu His Trp Tyr Gln Gln Lys Pro Gly Lys Ala Pro Lys Leu Leu
 1               5                  10                  15

Ile Tyr Glu Ala Ser Ser Leu
                20

<210> SEQ ID NO 70
<211> LENGTH: 15
<212> TYPE: PRT
<213> ORGANISM: Aotus trivirgatus
<220> FEATURE:
<221> NAME/KEY: VARIANT
<222> LOCATION: 1
<223> OTHER INFORMATION: Xaa = Any Amino Acid

<400> SEQUENCE: 70

Xaa Leu Ile Tyr Glu Ala Ser Ser Leu Gln Ser Gly Val Pro Ser
 1               5                  10                  15

<210> SEQ ID NO 71
<211> LENGTH: 108
<212> TYPE: PRT
<213> ORGANISM: Aotus trivirgatus
```

```
<400> SEQUENCE: 71

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Ser Ile Asp Ser Tyr
            20                  25                  30

Leu His Trp Tyr Gln Gln Lys Pro Gly Lys Ala Pro Lys Leu Leu Ile
        35                  40                  45

Tyr Glu Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Val Val Trp Arg Pro Phe
                85                  90                  95

Thr Phe Gly Gln Gly Thr Lys Val Glu Ile Lys Arg
            100                 105

<210> SEQ ID NO 72
<211> LENGTH: 23
<212> TYPE: PRT
<213> ORGANISM: Callithrix, species unknown
<220> FEATURE:
<221> NAME/KEY: VARIANT
<222> LOCATION: 1
<223> OTHER INFORMATION: Xaa = Any Amino Acid

<400> SEQUENCE: 72

Xaa Leu His Trp Tyr Gln Gln Lys Pro Gly Lys Ala Pro Lys Leu Leu
 1               5                  10                  15

Ile Tyr Glu Ala Ser Lys Leu
            20

<210> SEQ ID NO 73
<211> LENGTH: 15
<212> TYPE: PRT
<213> ORGANISM: Callithrix, species unknown
<220> FEATURE:
<221> NAME/KEY: VARIANT
<222> LOCATION: 1
<223> OTHER INFORMATION: Xaa = Any Amino Acid

<400> SEQUENCE: 73

Xaa Leu Ile Tyr Glu Ala Ser Lys Leu Gln Ser Gly Val Pro Ser
 1               5                  10                  15

<210> SEQ ID NO 74
<211> LENGTH: 108
<212> TYPE: PRT
<213> ORGANISM: Callithrix, species unknown

<400> SEQUENCE: 74

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Ser Ile Asp Ser Tyr
            20                  25                  30

Leu His Trp Tyr Gln Gln Lys Pro Gly Lys Ala Pro Lys Leu Leu Ile
        35                  40                  45

Tyr Glu Ala Ser Lys Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Val Val Trp Arg Pro Phe
```

```
                        85                  90                  95

Thr Phe Gly Gln Gly Thr Lys Val Glu Ile Lys Arg
            100                 105

<210> SEQ ID NO 75
<211> LENGTH: 24
<212> TYPE: PRT
<213> ORGANISM: Callithrix, species unknown
<220> FEATURE:
<221> NAME/KEY: VARIANT
<222> LOCATION: 1
<223> OTHER INFORMATION: Xaa = Any Amino Acid

<400> SEQUENCE: 75

Xaa Leu His Trp Tyr Gln Gln Lys Pro Gly Lys Ala Pro Lys Ser Leu
1               5                   10                  15

Leu Ile Tyr Ser Ala Ser Asn Leu
            20

<210> SEQ ID NO 76
<211> LENGTH: 16
<212> TYPE: PRT
<213> ORGANISM: Callithrix, species unknown
<220> FEATURE:
<221> NAME/KEY: VARIANT
<222> LOCATION: 1, 16
<223> OTHER INFORMATION: Xaa = Any Amino Acid

<400> SEQUENCE: 76

Xaa Leu Ile Tyr Ser Ala Ser Asn Leu Glu Thr Gly Val Pro Ser Xaa
1               5                   10                  15

<210> SEQ ID NO 77
<211> LENGTH: 108
<212> TYPE: PRT
<213> ORGANISM: Callithrix, species unknown

<400> SEQUENCE: 77

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Asp Ser Tyr
            20                  25                  30

Leu His Trp Tyr Gln Gln Lys Pro Gly Lys Ala Pro Lys Leu Leu Ile
        35                  40                  45

Tyr Ser Ala Ser Asn Leu Glu Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Val Val Trp Arg Pro Phe
                85                  90                  95

Thr Phe Gly Gln Gly Thr Lys Val Glu Ile Lys Arg
            100                 105
```

The invention claimed is:

1. A recombinant domain antibody (dAb) which binds to human TNF-α, wherein the dAb has a sequence selected from the group consisting of:

(SEQ ID No: 8)
DIQMTQSPSSLSASVGDRVTITCRASQAIDSYLHWYQQKPGKAPKLLIYS
ASNLETGVPSRFSGSGSGTDFTLTISSLQPEDFATYYCQQVVWRPFTFGQ
GTKVEIKR;

(SEQ ID No: 9)
DIQMTQSPSSLSASVGDRVTITCRASQSIDSYLHWYQQKPGKAPKLLIYS
ASNLETGVPSRFSGSGSGTDFTLTISSLLPEDFATYYCQQVVWRPFTFGQ
GTKVEIKR;

(SEQ ID No: 10)
DIQMTQSPSSLSASVGDRVTITCRASQAIDSYLHWYQQKPGKAPKLLIYS
ASNLETGVPSRFSGSGSGTDFTLTISSLLPEDFATYYCQQVVWRPFTFGQ
GTKVEIKR;

(SEQ ID No: 50)
DIQMTQSPSSLSASVGDRVTITCRASQSIDSYLHWYQQKPGKPPKLLIYS
ASNLETGVPSRFSGSGSGTDFTLTISSLQPEDFATYYCQQVVWRPFTFGQ
GTKVEIKR;

(SEQ ID No: 51)
DIQMTQSPSSLSASVGDRVTITCRASQSIDSYLHWYQQKPGKAPKLLIYS
ASNLETGVPSRFSGRGSGTDFTLTISSLQPEDFATYYCQQVVWRPFTFGQ
GTKVEIKR;
and (SEQ ID No: 52)
DIQMTQSPSSLSASVGDRVTITCRASQSIDSYLHWYQQKPGKAPKLLIYS
ASNLETGVPSRFSGSGSGTDFTLTISSLVPEDFATYYCQQVVWRPFTFGQ
GTKVEIKR.

2. A recombinant dAb according to claim 1 wherein the dAb has the sequence:

(SEQ ID No: 10)
DIQMTQSPSSLSASVGDRVTITCRASQAIDSYLHWYQQKPGKAPKLLIYS
ASNLETGVPSRFSGSGSGTDFTLTISSLLPEDFATYYCQQVVWRPFTFGQ
GTKVEIKR.

3. A pharmaceutical composition comprising an effective amount of a recombinant domain antibody (dAb) according to claim 1, together with a pharmaceutically acceptable carrier or diluent.

4. A method for detecting human TNF-α in a sample comprising contacting the sample with an effective amount of a recombinant dAb according to claim 1 and detecting the amount of bound dAb.

5. The method according to claim 4 wherein the sample is a biological sample.

6. A recombinant dAb according to claim 1 wherein the dAb has the sequence:

(SEQ ID No: 8)
DIQMTQSPSSLSASVGDRVTITCRASQAIDSYLHWYQQKPGKAPKLLIYS
ASNLETGVPSRFSGSGSGTDFTLTISSLQPEDFATYYCQQVVWRPFTFGQ
GTKVEIKR.

7. A recombinant dAb according to claim 1 wherein the dAb has the sequence:

(SEQ ID No: 9)
DIQMTQSPSSLSASVGDRVTITCRASQSIDSYLHWYQQKPGKAPKLLIYS
ASNLETGVPSRFSGSGSGTDFTLTISSLLPEDFATYYCQQVVWRPFTFGQ
GTKVEIKR.

8. A recombinant dAb according to claim 1 wherein the dAb has the sequence:

(SEQ ID No: 50)
DIQMTQSPSSLSASVGDRVTITCRASQSIDSYLHWYQQKPGKPPKLLIYS
ASNLETGVPSRFSGSGSGTDFTLTISSLQPEDFATYYCQQVVWRPFTFGQ
GTKVEIKR.

9. A recombinant dAb according to claim 1 wherein the dAb has the sequence:

(SEQ ID No: 51)
DIQMTQSPSSLSASVGDRVTITCRASQSIDSYLHWYQQKPGKAPKLLIYS
ASNLETGVPSRFSGRGSGTDFTLTISSLQPEDFATYYCQQVVWRPFTFGQ
GTKVEIKR.

10. A recombinant dAb according to claim 1 wherein the dAb has the sequence:

(SEQ ID No: 52)
ADIQMTQSPSSLSASVGDRVTITCRASQSIDSYLHWYQQKPGKAPKLLIY
SASNLETGVPSRFSGSGSGTDFTLTISSLVPEDFATYYCQQVVWRPFTFG
QGTKVEIKR.

* * * * *